US006407063B1

(12) United States Patent
Luiten et al.

(10) Patent No.: US 6,407,063 B1
(45) Date of Patent: Jun. 18, 2002

(54) TUMOR ANTIGENS AND CTL CLONES ISOLATED BY A NOVEL PROCEDURE

(75) Inventors: Rosalie Luiten; Marie-Therese Duffour; Nathalie Demotte; Pierre van der Bruggan; Guy Cornelius; Vincent Stroobant; Christophe Lurquin; Thierry Boon-Falleur, all of Brussels (BE)

(73) Assignees: Ludwig Institute for Cancer Research, New York, NY (US); Universite Catholique de Louvain, Louvain-la-Neuve (BE)

( * ) Notice: Subject to any disclaimer, the term of this patent is extended or adjusted under 35 U.S.C. 154(b) by 0 days.

(21) Appl. No.: 09/165,863

(22) Filed: Oct. 2, 1998

(51) Int. Cl.$^7$ ................ A61K 38/08; A61K 38/10; C07K 7/06; C07K 7/08

(52) U.S. Cl. ................ 514/13; 530/326; 530/328; 514/15

(58) Field of Search .............. 514/15, 13; 530/328, 530/326

(56) References Cited

U.S. PATENT DOCUMENTS

| | | | |
|---|---|---|---|
| 4,769,330 A | 9/1988 | Paoletti | |
| 5,342,774 A | 8/1994 | Boon et al. | |
| 5,558,995 A | 9/1996 | van der Bruggen | |
| 5,925,729 A | * 7/1999 | Boon et al. | 530/328 |

FOREIGN PATENT DOCUMENTS

| | | |
|---|---|---|
| WO | WO 94/03205 | 2/1994 |
| WO | WO 95/04542 | 2/1995 |
| WO | WO 95/21630 | 8/1995 |
| WO | WO 98/10780 | 3/1998 |
| WO | WO 99/14326 | 3/1999 |
| WO | WO 99/45954 | 9/1999 |

OTHER PUBLICATIONS

Cox et al. (1993) "Induction of Cytotoxic T Lymphocytes by Recombinant Canarpox (ALVAC) and Attenuated Vaccinia (NYVAC) Viruses Expressing the HIV–1 Envelope Glycoprotein", *Virology* 195: 845–850.

Kim et al. (1997) "Dendritic Cells Infected with Poxviruses Encoding MART–1/Melan A Sensitize T Lymphocyts In Vitro", *Journal of Immunotherapy* 20 (4): 276–286.

Knuth et al. (1989) "Cytolytic T–cell clones against an autologous human melanoma: Specificty study and definition of three antigens by immunoselection", *Proc. Natl. Acad. Sci. USA* 86: 2804–2808.

Rüssmann et al. (1998) "Delivery of Epitopes by the Salmonella Type III Secretion System for Vaccine Development", *Science* 281: 565–568.

Sory et al. (1994) "Translocation of a hybrid YopE–adenylate cyclase from *Yersinia enterocolitica* into HeLa cels", *Molecular Microbiology* 14(3): 583–594.

Van den Eynde et al. (1989) "Presence On A Human Melanoma of Multiple antigens Recognized by Autologous CTL", *Int. J. Cancer* 44: 634–640.

Etienne De Plaen, et al. (1994) "Structure, chromosomal localization, and expression of 12 genes of the MAGE family", *Immunogentics* 40: 360–369.

Darryl S. Reed, et al. (1997) "Construction and characterization of a recombinant adneovirus directing expression of the MAGE–1 tumor–specific antigen", *Int. J. Cancer* 72: 1045–1055.

* cited by examiner

*Primary Examiner*—David Saunders
(74) *Attorney, Agent, or Firm*—Scully, Scott, Murphy & Presser

(57) ABSTRACT

The present invention relates to isolation of cytotoxic T lymphocyte (CTL) clones. In particular, the present invention relates to isolated CTL clones that are specific for MAGE-1 and MAGE-4, respectively. The CTL clones of the present invention have been isolated by successive steps of stimulation and testing of lymphocytes with antigen presenting cells which present antigens derived from different expression systems, e.g., from recombinant Yersinia, recombinant Salmonella, or recombinant viruses. The present invention further relates to the MAGE-1 and MAGE-4 antigenic peptides as well as the peptide/HLA complexes which are recognized by the isolated CTL clones.

8 Claims, 11 Drawing Sheets

A — — — — — — — — — — — — — — — — — A

AACTACCTGGAGTACCGGCAGGTACCCGGCAGTAATCCTGCGCGCTAT

GAGTTCCTGTGGGGTCCAAGGGCTCTGGCTGAAACCAGCTATGTGAAA
　　　　　AS2

GTCCTGGAGCATGTGGTCAGGGTCAATGCAAGAGTTCGCATTGCCTAC

CCATCCCTGCGTGAAGCAGCTTTGTTAGAGGAGGAAGAGGGAGTCTGA
　　　　　　　　　　　　　　　　AS1

Figure 6B

```
AGTCATCATGTCTTCTGAGCAGAAGAGTCAGCACTGCAAGCCTGAGGA
                    S

AGGCGTTGAGGCCCAAGAAGAGGCCCTGGGCCTGGTGGGTGCACAGGC
                  AS8

TCCTACTACTGAGGAGCAGGAGGCTGCTGTCTCCTCCTCCTCTCCTCTG

GTCCCTGGCACCCTGGAGGAAGTGCCTGCTGCTGAGTCAGCAGGTCCTC
                        AS7

CCCAGAGTCCTCAGGGAGCCTCTGCCTTACCCACTACCATCAGCTTCA

CTTGCTGGAGGCAACCCAATGAGGGTTCCAGCAGCCAAGAAGAGGAGG

GGCCAAGCACCTCGCCTGACGCAGAGTCCTTGTTCCGAGAAGCACTCA
           AS6

GTAACAAGGTGGATGAGTTGGCTCATTTTCTGCTCCGCAAGTATCGAG

CCAAGGAGCTGGTCACAAAGGCAGAAATGCTGGAGAGAGTCATCAAA

AATTACAAGCGCTGCTTTCCTGTGATCTTCGGCAAAGCCTCCGAGTCC
     AS5

CTGAAGATGATCTTTGGCATTGACGTGAAGGAAGTGGACCCCGCCAGC

AACACCTACACCCTTGTCACCTGCCTGGGCCTTTCCTATGATGGCCTG
                         AS4

CTGGGTAATAATCAGATCTTTCCCAAGACAGGCCTTCTGATAATCGTC

CTGGGCACAATTGCAATGGAGGGCGACAGCGCCTCTGAGGAGGAAATC

TGGGAGGAGCTGGGTGTGATGGGGGTGTATGATGGGAGGGAGCACACT
          AS3

GTCTATGGGGAGCCCAGGAAACTGCTCACCCAAGATTGGGTGCAGGAA
```

TUMOR ANTIGENS AND CTL CLONES ISOLATED BY A NOVEL PROCEDURE

FIELD OF INVENTION

The present invention relates to isolation of cytotoxic T lymphocyte (CTL) clones. In particular, the present invention relates to isolated CTL clones that are specific for MAGE-1 and MAGE-4, respectively. The CTL clones of the present invention have been isolated by successive steps of stimulation and testing of lymphocytes with antigen presenting cells which present antigens derived from different expression systems, e.g., from recombinant Yersinia, recombinant Salmonella, or recombinant viruses. The present invention further relates to the MAGE-1 and MAGE-4 antigenic peptides as well as the peptide/HLA complexes which are recognized by the isolated CTL clones.

BACKGROUND

An important facet of the immune response in a mammalian subject is the recognition by T cells of the complexes of the cell surface molecules, i.e., the complexes of peptides and HLA (human leukocyte antigens) or MHC (major histocompatibility complexes) molecules. These peptides are derived from larger molecules which are processed by the cells which also present the HLA/MHC molecules. See in this regard, Male et al., *Advanced Immunology* (J. P. Lipincott Company, 1987), especially chapters 6–10. The interaction between T cell and HLA/peptide complexes is restricted, requiring a T cell specific for a particular combination of an HLA molecule and a peptide. If a specific T cell is not present, there is no T cell response even if its partner complex is present. Similarly, there is no response if the specific complex is absent, but the T cell is present. This mechanism is involved in the immune system response to foreign materials, in autoimmune pathologies, and in responses to cellular abnormalities.

Most progressively growing neoplastic cells express potentially immunogenic tumor-associated antigens (TAAs), also called tumor rejection antigens (TRAs). A number of genes have been identified that encode tumor rejection antigen precursors (or TRAPs), which are processed into TRAs in tumor cells. Such TRAP-encoding genes include members of the MAGE family, the BAGE family, the DAGE/Prame family, the GAGE family, the RAGE family, the SMAGE family, NAG, Tyrosinase, Melan-A/MART-1, gp 100, MUC-1, TAG-72, CA125, mutated proto-oncogenes such as praise, mutated tumor suppressor genes such as p53, tumor associated viral antigens such as HPV16 E7. See, e.g., review by Van den Eynde and van der Bruggen (1997) in *Curr. Opin. Immunol.* 9:684–693, Sahin et al. (1997) in *Curr. Opin. Immunol.* 9:709–716, and Shawler et al. (1997) *Advances in Pharmacology* 40: 309–337, Academic Press, Inc., San Diego, Calif.

TRAs, like other antigenic epitopes, are presented at the surface of tumor cells by MHC molecules and have been shown to induce a CTL response in vivo and in vitro. See, for example, van der Bruggen et al. (1991) *Science* 254: 1643–1647. However, such TRA-expressing tumor cells do not provoke reliable anti-tumor immune responses in vivo that are capable of controlling the growth of malignant cells. Boon et al. (1992) *Cancer Surveys* 13: 23–37; T. Boon (1993) *Int. J. Cancer* 54: 177–180; T. Boon (1992) *Advances Cancer Res.* 58: 177–209. Thus, generation of CTL clones that recognize specific TRAs provides a powerful tool for tumor therapeutics. The identification of TRAs also allows the design of recombinant vaccines for the treatment of various pathological conditions.

The present invention provides isolated CTL clones that are specific for MAGE-1 and MAGE-4, respectively. These CTL clones have been isolated by successive steps of stimulation and testing of lymphocytes with antigen presenting cells which present antigens derived from different expression system, e.g., from recombinant Yersinia or recombinant viruses. The MAGE-1 and MAGE-4 antigenic peptides which are recognized by these CTL clones, as well as the presenting MHC molecules, have also been identified by the present invention.

SUMMARY OF THE INVENTION

The present invention relates to isolation of CTL clones. The present invention further relates to newly isolated CTL clones, tumor associated antigens and peptide/HLA complexes.

One embodiment of the present invention provides methods for generating specific CTLs in vitro or ex vivo by successive stimulations and tests of lymphocytes with antigen presenting cells which present antigens derived from different expression systems.

More specifically, the present method for isolating CTL clones includes multiple steps of stimulation and testing with antigen presenting cells. The antigen presenting cells in different steps of stimulation can differ from one another in cell types and in the manner by which the antigen is derived. The use of different antigen presenting cells as stimulator cells reduces CTL activities that are non-specific for the protein of interest, and thus, permits more efficient isolation of specific CTL clones.

In accordance with the present invention, the antigen can derive from a protein expressed from recombinant Yersinia, recombinant Salmonella, or recombinant viruses, respectively. The recombinant virus can be made using strains of vaccinia, canarypox virus, other pox viruses, adenovirus, herpes simplex virus and the like.

The protein against which specific CTL clones are generated can be a tumor associated protein, an antigenic protein of a pathogen, or the like. More preferably, the protein is MAGE-1 or MAGE-4.

In another embodiment, the present invention provides CTL clones generated by using the method of the present invention. Specifically, the present invention provides three newly isolated CTL clones, clone 462/F3.2, which specifically recognizes a MAGE-1 peptide (230–238) presented by HLA-Cw3; clone 456/H7.11, which specifically recognizes a MAGE-1 epitope (258–266) presented by HLA-B53, and clone H4/13, which specifically recognizes a MAGE-4 epitope (230–239) presented by HLA-A2.

In still another embodiment, the present invention provides isolated antigenic peptides, DPARYEFLW (MAGE-1 258–266) (SEQ ID NO:42) and GVYDGREHTV (MAGE-4 230–239) (SEQ ID NO:44), as well as nucleic acid sequences encoding thereof.

In another embodiment, the present invention provides isolated peptide/HLA complexes, peptide SAYGEPRKL (MAGE-1 230–238) (SEQ ID NO:2) complexed with HLA-Cw3, peptide DPARYEFLW (MAGE-1258–266) (SEQ ID NO:42) complexed with HLA-B53, and peptide GVYDGREHTV (MAGE-4 230–239) (SEQ ID NO:44) complexed with HLA-A2. Cells expressing any of the peptide/HLA complexes are also contemplated.

The isolated CTL clones, the antigenic peptides, the peptide/HLA complexes, and cells expressing the peptide/HLA complexes of the present invention can be used in pharmaceutical compositions as well as methods for diagnosing and treating various pathological conditions.

Figure 1:
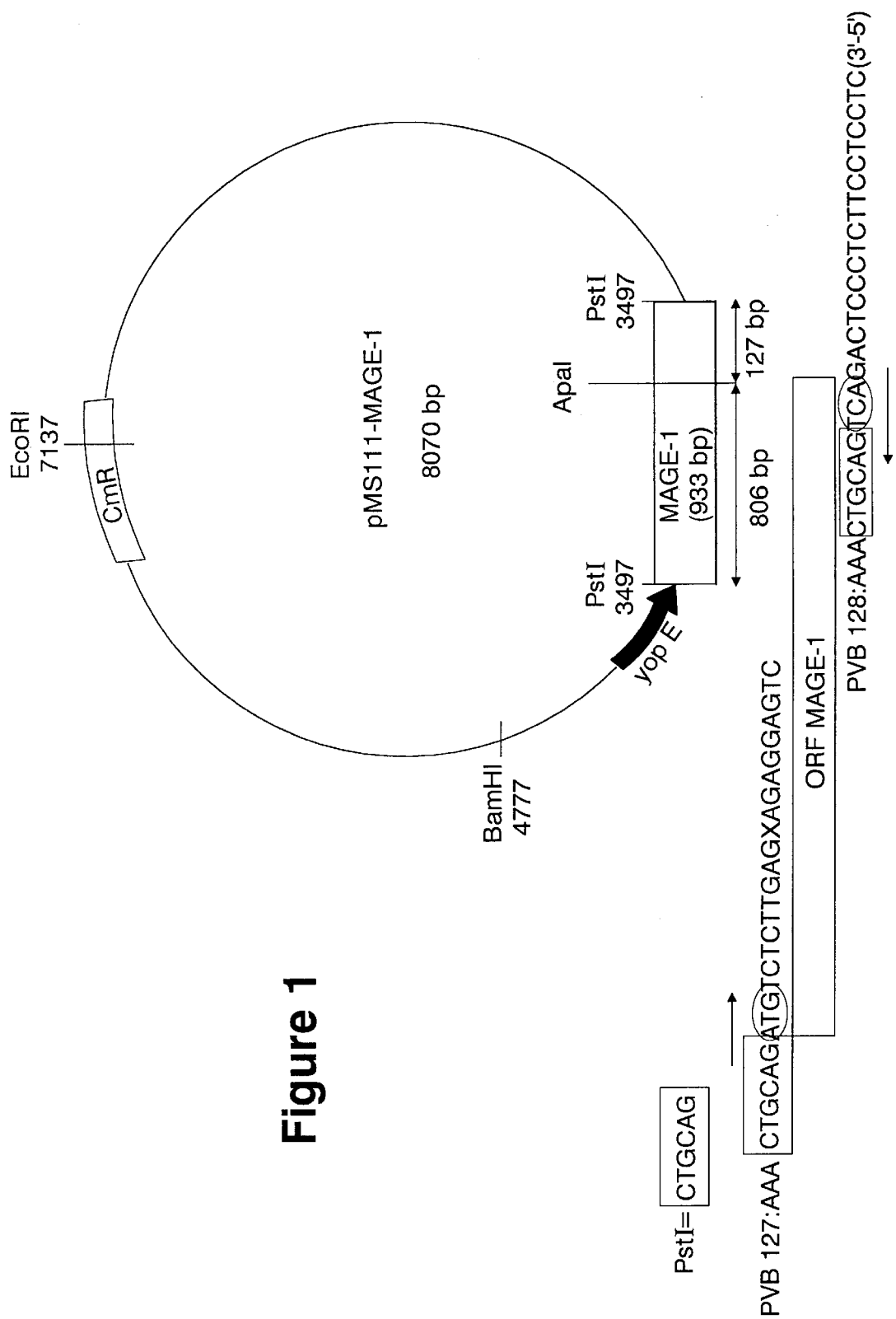
FIG. 1 illustrates the plasmid map of the expression vector pMS111-MAGE-1 ($YopE_{130}$-MAGE1).

FIGS. 4A–4C depict the specific recognition by CTL clone 456/H7.11 of a MAGE-1 antigenic peptide presented by HLA-B53.

FIGS. 5A–5D depict the specific recognition by CTL clone H4/13 of a MAGE-4 antigenic peptide presented by HLA-A2.

FIG. 6 depicts the MAGE-4 nucleotide sequences and the primers used in PCR as described in Example 9.

DETAILED DESCRIPTION OF THE INVENTION

One embodiment of the present invention provides methods for generating specific CTLs in vitro or ex vivo by successive steps of stimulation and testing of lymphocytes with antigen presenting cells which present antigens derived from different expression systems.

The procedure to develop specific CTL clones in vitro is known in the art, e.g., as disclosed by the U.S. Pat. No. 5,342,774, Knuth et al. (*Proc. Natl. Acad. Sci. USA* 86: 2804–2808, 1989) and Van Den Eynde et al. (*Int. J. Cancer* 44: 634–640, 1989). Briefly, a blood sample containing T cell precursors is taken from a mammal. PBLs are purified from such blood sample and are incubated with stimulator cells expressing an antigenic epitope in the context of an MHC molecule. Additional components, e.g.., allogeneic feeder cells and cytokines, can be added into the incubation mixture. CTLs that are specific for the epitope proliferate, and thus, are enriched in response to such stimulation. Such specific CTLs can be detected by standard assays a $^{51}Cr$ release assay, a IFN-γ secretion assay, or a TNF production assay. Specific CTL clones can be subsequently obtained by, e.g., limiting dilution.

In accordance with the present invention, specific CTL clones can be isolated by successive steps of stimulation and testing, with different antigen presenting cells as stimulator cells, of samples containing T cell precursors. In particular, the antigen presenting cells may differ from one another in cell types and in the expression systems from which the antigen is derived. The use of different stimulator cells in each step of stimulation and testing allows the reduction of CTL responses against non-specific molecules, e.g., molecules expressed from the backbone sequence of an expression vector; whereas specific CTLs against the antigen of interest are enriched.

"Antigen presenting cells" as referred herein, express at least one class I or class II MHC determinant and may include those cells which are known as professional antigen-presenting cells such as macrophages, dendritic cells and B cells. Other professional antigen-presenting cells include monocytes, marginal zone Kupffer cells, microglia, Langerhans' cells, interdigitating dendritic cells, follicular dendritic cells, and T cells. Facultative antigen-presenting cells can also be used according to the present invention. Examples of facultative antigen-presenting cells include activated T cells, astrocytes, follicular cells, endothelium and fibroblasts. As used herein, "antigen-presenting cells" encompass both professional and facultative types of antigen-presenting cells.

The antigen presenting cells can be isolated from tissue or blood (containing peripheral blood mononuclear cells) samples obtained from a mammal such as human. Cell lines established from such samples may also be used. Procedures for establishing cell lines are well known in the art. Certain cell lines may be obtained directly from the American Type Culture Collection, 10801 University Boulevard, Manassas, Va. 20110-2209. Both normal and malignant cells can be employed.

In accordance with the present invention, the MHC determinants expressed by the antigen presenting cells are compatible with those expressed by the mammal from which the sample containing T cell precursors is taken. Preferably, autologous antigen presenting cells or cell lines established therefrom are employed. No-autologous cells may be used as long as the MHC determinants expressed by such cells are compatible, either naturally, by way of transfection or by some other means. One skilled in the art is also familiar with the methods for determining whether the MHC molecules expressed by the antigen presenting cell are compatible with those of the mammal subject involved, such as well known HLA-typing procedures. See general teachings by Coligan et al. (1994) *Current Protocols in Immunology* John Wiley & Sons Inc: New York, N.Y.

Further according to the present invention, the antigen presenting cells can also differ in the manner by which the antigens of interest are derived. More specifically, the antigens against which specific CTLs are generated, can derive from a protein which is produced by an expression system, e.g., a recombinant Yersinia, a recombinant Salmonella, or a recombinant virus.

According to the present invention, a protein of interest can be expressed in a recombinant Yersinia and delivered into the cytosol of the antigen presenting cells for processing and presentation.

The term "Yersinia" as used herein includes all species of Yersinia, including *Yersinia enterocolitica, Yersinia pseudotuberculosis* and *Yersinia pestis.* The term "recombinant Yersinia" used herein refers to Yersinia genetically transformed with an expression vector. The term "delivery" used herein refers to the transportation of a protein from a Yersinia to an antigen presenting cell, including the steps of expressing the protein in the Yersinia, secreting the expressed protein(s) from such Yersinia and translocating the secreted protein(s) by such Yersinia into the cytosol of the antigen presenting cell.

According to the present invention, preferred Yersinia for use in expressing and delivering the protein of interest are mutant Yersinia that are deficient in producing functional effector proteins.

A preferred mutant Yersinia strain for use in expressing and delivering the protein of interest is a quintuple-mutant Yersinia strain in which all the effector-encoding genes are mutated such that the resulting Yersinia no longer produce any functional effector proteins. Such quintuple-mutant Yersinia strain is designated as yopEHOMP for *Y. enterocolitica* or yopEHAM for *Y. pseudotuberculosis.* One example of such yopEHOMP strain is *Y. enterocolitica* MRS40(pABL403).

The protein of interest can be cloned into an yersinia expression vector Ffr use in combination with a mutant Yersinia for delivery of the protein into antigen presenting cells. In accordance with the present invention, such a vector is characterized by (in the 5' to 3' direction) a promoter, a first nucleic acid sequence encoding a delivery signal, a second nucleic acid sequence fused thereto coding for the protein to be delivered and other sequences that may be appropriate (e.g., a polyadenylation signal).

The promoter of the expression vector is preferably from a Yersinia virulon gene. A "Yersinia virulon gene" refers to genes on the Yersinia pYV plasmid, the expression of which is controlled both by temperature and by contact with a target cell. See review by Cornelis et al. (1997). Such genes include genes coding for elements of the secretion machinery (the Ysc genes), genes coding for translocators (YopB, YopD, and LcrV), genes coding for the control elements (YopN and LcrG), and genes coding for effectors (YopE, YopH, YopO/YpkA, YopM and YopP/YopJ). Preferably, the promoter is from an effector-encoding gene selected from any one of YopE, YopH, YopO/YpkA, YopM and YopP/YopJ. More preferably, the promoter is from YopE.

Further in accordance with the present invention, a first DNA sequence coding for a delivery signal is operably linked to the promoter. "A delivery signal", as described hereinabove, refers to a polypeptide which can be recognized by the secretion and translocation system of Yersinia and therefore directs the secretion and translocation of a protein into a an antigen presenting cell. Such polypeptide is from an effector protein including YopE, YopH, YopO/YpkA, YopM, and YopP/YopJ, and preferably, YopE. More preferably, the effector protein is YOpE of *Yersinia enterocolitica*.

One skilled in the art is familiar with the methods for identifying the polypeptide sequences of an effector protein that are capable of delivering a protein. For example, one such method is described by Sory et al. (1994). Examples of such delivery signal polypeptides include from *Y. enterocolitica:* $YopE_{130}$ (the N-terminal 130 amino acids of YopE), $YopE_{50}$, $YopM_{100}$ and $YopH_{71}$.

The yersinia expression vectors may be transformed into Yersinia by a number of known methods which include, but are not limited to, electroporation, calcium phosphate mediated transformation, conjugation, or combinations thereof. For example, a vector can be transformed into a first bacteria strain by a standard electroporation procedure. Subsequently, such a vector can be transferred from the first bacteria strain into Yersinia by conjugation, a process also called "mobilization". Yersinia transformant (i.e., Yersinia having taken up the vector) may be selected, e.g., with antibiotics. These techniques are well known in the art. See, for example, Sory et al. (1994).

The delivery of a protein from a recombinant Yersinia into the cytosol of an antigen presenting cell can be effected by contacting an antigen presenting cell with a recombinant Yersinia under appropriate conditions. Multiple references and techniques are available for those skilled in the art regarding the conditions for inducing the expression and translocation of virulon genes, including the desired temperature, Ca++ concentration, manners in which Yersinia and target cells are mixed, and the like. See, for example, Cornelis, Cross talk between Yersinia and eukaryotic cells, Society for General Microbiology Symposium, 55; Mocrae, Saunders, Smyth, Stow (eds), *Molecular aspects of host-pathogen interactions,* Cambridge University Press, 1997. The conditions may vary depending on the type of eukaryotic cells to be targeted, e.g.: the conditions for targeting human epithelial carcinoma Hela cells (Sory et al. (1994)); the conditions for targeting mouse thymoma or melanoma cells (Starnbach et al. (1994) *J. Immunol.* 153: 1603); and the conditions for targeting mouse macrophages (Boland et al. (1996)). Such variations can be addressed by those skilled in the art using conventional techniques.

Those skilled in the art can also use a number of assays to determine whether the delivery of a fusion protein is successful. For example, the fusion protein may be labeled with an isotope or an immunofluoresceine, or detected by a immunofluoresceine conjugated antibody, as disclosed by Rosqvist et al. (1994) *EMBO J.* 13: 964. The determination can also be based on the enzymatic activity of the protein being delivered, e.g., the assay described by Sory et al. (1994). The determination can also be based on the antigenicity of the protein being delivered. For example, the delivery of a MAGE-1 protein into EBV-transformed human B cells can be detected by the recognition of such targeted B cells by CTL cells specific for MAGE-1 epitopes. Such CTL recognition, in turn, may be detected by a number of assays including assaying the secretion of IFN-γ from the activated CTLs or $Cr^{51}$ release from lysed target cells. Methods such as Western-blot analysis using antibodies specific against the protein being delivered, PCR in situ hybridization, or ELISPOT (Mabtech AB, Sweden) may also be employed for such determination. See, e.g., W. Herr et al. (1997) *J. Immunol.* Methods 203: 141–152 and W. Herr et al. (1996) *J. Immunol.* Methods 191: 131–142.

In accordance with the present invention, the protein of interest can also be expressed from a recombinant Salmonella. For example, avirulent strains of *Salmonella typhimurium* can be used as antigen delivery vectors. It is known in the art that antigenic epitopes, such as viral epitopes can be successfully delivered to the host cell cytosol by using the type III protein secretion system of *S. typhimurium.* See, e.g., Russmann et al. (1998) 281: 565–568.

In accordance with the present invention, the expression of a protein of interest in the antigen presenting cell can also be effected by a recombinant virus. In particular, the present invention contemplates recombinant viruses of vaccinia, canarypox virus, other pox viruses, adenovirus, herpes simplex virus and the like.

A preferred strain of vaccinia for use in the present invention is the WR strain (Panicali et al.(1981), *J. Virol.* 37: 1000–1010). The nucleotide sequence coding for the protein of interest can be operably linked to a promoter, such as an vaccinia promoter H6, and inserted into a vaccinia vector, thereby generating a donor plasmid. Vaccinia vectors which can be employed for generating adeno-plasmid are available to those skilled in the art and are described in, e.g., U.S. Pat. No. 4,769,330. Recombinant WR strains of vaccinia can be generated by using a donor plasmid via in vivo recombination, following well-known procedures. See, e.g., Perkins et al., *J. Virol.* 63: 3829–3936 (1989).

A preferred strain of canarypox virus for use in the present invention is ALVAC (Cox et al. (1993), *Virology* 195: 845–850). The nucleotide sequence coding for the protein of interest can be operably linked to a promoter, such as an vaccinia promoter H6, and inserted into an ALVAC vector to create a donor plasmid. Multiple ALVAC vectors are available to one skilled in the art and are described by, e.g., U.S. Pat. No. 5,756,106; Cox et al. (1993) *Virology* 195: 845–850; Tartaglia et al. (1993) *J. Virology* 67: 2370–2375; and Taylor et al. (1992) *Virology* 187: 321–328. Such donor plasmid can be used to generate recombinant ALVAC viruses via in vivo recombination. See, e.g., Cox. et al. (1993); Tartaglia et al. (1993) and Taylor et al. (1992).

Those skilled in the art can also generate recombinant adenoviruses for expressing the protein of interest as described in, e.g., Example 5 hereinafter.

A nucleotide sequence encoding the protein of interest can be cloned into the various expression vectors as described above. There is no particular limitation in the protein that can be presented by antigen presenting cells in the instant methods for isolating CTL clones. The term "protein" as used herein refers to naturally occurring proteins as well as artificially engineered proteins, or parts thereof. The term "part of a protein" includes a peptide fragment of a protein that is of sufficient length to be antigenic. Preferably, such a fragment consists of at least 8 or 9 contiguous amino acids of a protein. "Artificially engineered proteins" as used herein refer to non-naturally occurring proteins, e.g., fusion of two or more naturally occurring proteins or parts thereof, or polytopes (in-frame fusion of two or more epitopes) as exemplified by Thompson et al. (1995) in Proc. Natl. Acad. Sci. USA 92: 5845–5849.

The present invention particularly contemplates proteins such as known tumor associated proteins or known antigens of pathogens.

A "tumor associated protein" refers to a protein that is specifically expressed in tumors or expressed at an abnormal level in tumors relative to normal tissues. Such tumor associated proteins include, but are not limited to, members of the MAGE family, the BAGE family (such as BAGE-1), the DAGE/Prame family (such as DAGE-1), the GAGE family, the RAGE family (such as RAGE-1), the SMAGE family, NAG, Tyrosinase, Melan-A/ MART-1, gp100, MUC-1, TAG-72, CA125, mutated proto-oncogenes such as p21ras, mutated tumor suppressor genes such as p53, tumor associated viral antigens (e.g., HPV16 E7), HOM-MEL-40, HOM-MEL-55, NY-COL-2, HOM-HD-397, HOM-RCC-1.14, HOM-HD-21, HOM-NSCLC-11, HOM-MEL-2.4, and HOM-TES-11. Members of the MAGE family include, but are not limited to, MAGE-1, MAGE-2, MAGE-3, MAGE-4, MAGE-11. Members of the GAGE family include, but are not limited to, GAGE-1, GAGE-6. See, e.g., review by Van den Eynde and van der Bruggen (1997) in Curr. Opin. Immunol. 9: 684–693, Sahin et al. (1997) in Curr. Opin. Immunol. 9: 709–716, and Shawler et al. (1997). These proteins have been shown to associate with certain tumors such as melanoma, lung cancer, prostate cancer, breast cancer, renal cancer and others.

A number of known antigenic proteins from pathogens are also contemplated by the present invention. The pathogens can include viruses, bacteria, parasites and fungi. Specific examples of antigenic proteins characteristic of a pathogen include the influenza virus nucleoprotein (residues 218–226, as set forth in F. et al. (1997) J. Virol. 71: 2715–2721) antigens from Sendai virus and lymphocytic choriomeningitis virus (see, An et al. (1997) J. Virol. 71: 2292–2302), the B1 protein of hepatitis C virus (Bruna-Romero et al. (1997) Hepatology 25: 470–477), the virus envelope glycoprotein gp 160 of HIV (Achour et al. (1996) J. Virol. 70: 6741–6750), amino acids 252–260 or the circumsporozite protein of Plasmodium berghei (Allsopp et al. (1996) Eur. J. Immunol. 26: 1951–1958), the influenza A virus nucleoprotein (residues 366–374, Nomura et al. (1996) J. Immunol. Methods 193: 4149), the listeriolysin O protein of Listeria monocytogenes (residues 91–99, An et al. (1996) Infect. Immun. 64: 1685–1693), the E6 protein (residues 131–140, Gao et al. (1995) J. Immunol. 155: 5519–5526) and E7 protein (residues 21–28 and 48–55, Bauer et al. (1995) Scand. J. Immunol. 42: 317–323) of human papillomavirus type 16, the M2 protein of respiratory syncytial virus (residues 82–90 and 81–95, Hsu et al. (1995) Immunology 85: 347–350), the herpes simplex virus type 1 ribonucleotide reductase (see, Salvucci et al. (1995) J. Gen. Virol. 69: 1122–1131) and the rotavirus VP7 protein (see, Franco et al. (1993) J. Gen. Virol. 74: 2579–2586), P. falciparum antigens (causing malaria) and hepatitis B surface antigen (Gilbert et al. (1997) Nature Biotech. 15: 1280–1283).

A number of small antigenic peptides can also be employed in the present invention. One skilled in the art can readily determine the length of the fragments required to produce immunogenic peptides. Alternatively, the skilled artisan can also use coding sequences for peptides that are known to elicit specific T cell responses (either $CD4^+$ or $CD8^+$ T cells), such as tumor-associated antigenic peptides (TAA, also known as TRAS for tumor rejection antigens) as disclosed by U.S. Pat. Nos. 5,462,871, 5,558,995, 5,554,724, 5,585,461, 5,591,430, 5,554,506, 5,487,974, 5,530,096, 5,519,117. Examples of TRAs are provided in Table 1. See also review by Van den Eynde and van der Bruggen (1997) and Shawler et al. (1997). Antigenic peptides of a pathogen origin can also be used, such as those disclosed by Gilbert et al. (1997).

As described herein above, sequences coding for a full-length naturally occurring protein, a part of a naturally occurring protein, combinations of parts of a naturally occurring protein, or combinations of different naturally occurring proteins or parts from different proteins, may all be employed to be cloned into the expression vectors as described hereinabove.

The protein of interest is processed in the antigen presenting cells into small peptides, which are complexed with the appropriate MHC molecules and presented at the cell surface. In the present invention, peptides that are complexed with MHC molecules and presented at the cell surface are also referred to as "antigens".

In a preferred-embodiment, the present invention provides recombinant yersinia expression vectors, pMS111-$YopE_{130}$-MAGE1 and PMS111-$YopE_{130}$-MAGE4; recombinant vaccinia vectors, WR-MAGE1 and WR-MAGE4, recombinant canarypox viral vectors, ALVAC-MAGE-1; and recombinant adenoviral vector adeno-MAGE4.

According to the present invention, the present method for isolating CTL clones includes multiple steps of stimulation and testing with antigen presenting cells. The antigen presenting cells in different steps can differ from one another in cell types and in the expression by which the antigen is expressed. According to the present invention, one of the expression systems used by the antigen presenting cells in one step (either stimulation or testing), is different from at least one of the other expression systems used in another step. Preferably, the antigen presenting cells used in a stimulation step employ a different expression system from that used in the immediately following testing step. For testing the specificity of CTL responses after stimulation, antigen presenting cells expressing high amounts of class I HLA molecules are preferred, e.g., EBV-transformed B cells.

The present invention provides examples of the use of a combination of different antigen presenting cells in isolating specific CTL clones. According to the present invention, CD8+T lymphocytes obtained from an individual can be stimulated in microwells with autologous monocyte-derived dendritic cells infected with a recombinant ALVAC canarypoxvirus, or a recombinant adenovirus, encoding a protein of interest. After several stimulation, an aliquot of each microculture can then be tested for specific lysis of autologous EBV-B cells infected with a recombinant Vaccinia encoding the protein of interest. The positive microcultures can then be diluted and stimulated again with autologous EBV-B cells infected with a recombinant Yersinia encoding the protein of interest. Specific clones can be detected and thus isolated by testing for specific lysis of autologous EBV-B cells infected with a recombinant Vaccinia encoding the protein of interest. The present invention is not limited to the above combination of antigen presenting cells.

In a further aspect of the invention, specific CTL clones isolated by using the methods of the present invention are contemplated. Specifically, the present invention provides three newly isolated CTL clones, clone 462/F3.2, which specifically recognizes a MAGE-1 peptide (230–238) presented by HLA-Cw3, clone 456/H7.11, which specifically recognizes a MAGE-1 epitope (258–266) presented by HLA-B53, and clone H4/13, which specifically recognizes a MAGE-4 epitope (230–239) presented by HLA-A2.

CTL clones isolated according to the present method can be used to identify antigenic epitopes of a protein of interest. Accordingly, another embodiment of the present invention is directed to isolated antigenic peptides and peptide/HLA complexes which are recognized the isolated CTL clones of the present invention.

The present invention provides two newly identified antigenic peptides, DPARYEFLW (MAGE-1 258–266) (SEQ ID NO:42) and GVYDGREHTV (MAGE-4 230–239) (SEQ ID NO:44). Nucleic acid sequences encoding these peptides are also contemplated. The present invention has further determined that these peptides can be presented by HLA molecules HLA-B53 and HLA-A2, respectively, and can be recognized by CTL clones 456/H7.11 and H4/13, respectively. A third peptide, SAYGEPRKL (MAGE-1 230–238) (SEQ ID NO:2), has been previous identified (U.S. Pat. No. 5,558,995) and has been found to be presented by HLA-Cw16. However, the present invention has determined that a different HLA molecule, HLA-Cw3, can present peptide SAYGEPRKL to CTL clone 462/F3.2.

Accordingly, another embodiment of the present invention is directed to isolated peptide/HLA complexes. Specifically, the present invention provides three newly isolated peptide/HLA complexes, peptide SAYGEPRKL (MAGE-1 230–238) (SEQ ID NO:2) complexed with HLA-Cw3, peptide DPARYEFLW (MAGE-1 258–266) (SEQ ID NO:42) complexed with HLA-B53, and peptide GVYDGREHTV (MAGE-4 230–239) complexed with HLA-A2.

Given an isolated CTL clone that is specific for a protein, those skilled in the art can determine the antigen of such protein that is specifically recognized by such CTL clone and the MHC/HLA molecule for presentation of such antigen. For example, antigens of interest can be made available for binding to the MHC molecules under study by, e.g., co-transfection or peptide loading. The MHC/HLA molecules which bind to and present the antigens of interest can be detected by a variety of standard assays, such as immunoflowcytometry, assays for $^{51}$Cr release, TNF production or IFN-γ production, or ELI-spot analysis. See, for example, Schmitt et al. (1997) *J. Immunol. Methods* 210: 167–174; Lalvani et al. (1997) *J. Exp. Med.* 126: 859; and Dunbar et al. (1998) *Current Biology* 8: 413–416. Antigens that are specifically recognized by a CTL clone can be determined by a combination of approaches, such as recombinant cloning and expression, functional tests (e.g., $^{51}$Cr release, TNF production or IFN-γ production), or analysis of the potential of binding to a given HLA molecule by using the programs available at http://bimas.dcrt.nih.gov/molbio/hla_bind/index.html. Those skilled in the art are also referred to, for example, U.S. Pat. Nos. 5,405,940, 5,558,995 and 5,530,096, for relevant teachings.

The present invention further contemplates cells expressing any of the instant peptide/HLA complexes at the cell surface. Such cells can be made by, e.g., cotransfection as described in the Examples of the present disclosure.

In another embodiment, the present invention is contemplates pharmaceutical compositions which include the isolated CTL clones, the isolated antigenic peptides, the peptide/HLA complexes, of the present invention, or combinations thereof.

The pharmaceutical compositions of the present invention can include other substances such as cytokines, adjuvants and pharmaceutically acceptable carriers. As used herein, a therapeutically acceptable carrier includes any and all solvents, including water, dispersion media, culture from cell media, isotonic agents and the like that are non-toxic to the host. Preferably, it is an aqueous isotonic buffered solution with a pH of around 7.0. The use of such media and agents in therapeutic compositions is well known in the art. Except insofar as any conventional media or agent is incompatible with the semi-allogeneic immunogenic cells of the present invention, use of such conventional media or agent in the therapeutic compositions is contemplated. Supplementary active ingredients can also be incorporated into the compositions.

In a further aspect of the present invention, the isolated CTL clones, the isolated antigenic peptides, the peptide/HLA complexes of the present invention can be employed for diagnosing or treating a relevant pathological condition in a subject, preferably, a human subject.

The pathological conditions contemplated by the present invention include tumors and infections by pathogens such as bacteria, parasites, fungus or virus, and the like.

The term "treating" is used to refer to alleviating or inhibiting a pathological condition, e.g., inhibiting tumor growth or metastasis, reducing the size of a tumor, or diminishing symptoms of a pathogen infection, by e.g., eliciting an immune response.

In one embodiment, the isolated CTL clones of the present invention can be employed in identifying cells involved in a pathological condition which abnormally express the peptide/HLA complex which is specifically recognized by a CTL clone. For example, the present invention provides that CTL clone 462/F3.2 recognizes melanoma cells expressing both HLA-Cw3 and MAGE-1. Thus, CTL clone such as 462/F3.2 can be used in detecting the presence of, or identifying, tumor cells expressing the specific peptide/HLA complex. Cells which abnormally express the peptide/HLA complex recognized by a CTL clone can be identified by lysis of the cells when such cells are contacted with the CTL clone. Lysis can be detected by, e.g., standard assays such as Cr release, IFN-gamma secretion, or TNF production.

In another embodiment, the isolated peptide/HLA complexes of the present invention can be used to detect the presence of CTL cells in a sample from a subject, which CTL cells can specifically recognize the peptide/HLA complexes. The approaches for such detection have been described hereinabove.

Further in accordance with the present invention, the isolated CTL clones can be administered, in a therapy regimen of adoptive transfer, to a mammal a pathological condition characterized by an abnormal expression of the protein used in the delivery system. See teachings by Greenberg (1986) *J. Immunol.* 136 (5): 1917; Riddel et al. (1992) *Science* 257: 238; Lynch et al. (1991) *Eur. J. Immunol.* 21: 1403; and Kast et al. (1989) *Cell* 59: 603 for adoptive transfer. CTLs, by lysing the cells abnormally expressing such antigens, can alleviate or treat the pathological condition at issue such as a tumor and an infection with a parasite or a virus.

As described hereinabove, the isolated peptide/HLA complexes of the present invention are found at the surface of tumor cells. Therefore, these isolated antigenic peptides, as well as the peptide/HLA complexes, can be administered as vaccines to a subject for treating a pathological condition involving cells abnormally expressing such complexes at the surface. The pathological condition can be alleviated by, e.g., specific-immune responses elicited due to the administered peptide or peptide/HLA complexes.

For treatment purposes, the isolated CTL clones, the peptides or the peptide/HLA complexes, can be administered to a subject alone or in combination with other appropriate materials such as cytokine, adjuvant or a pharmaceutical carrier. The amount of the CTL cells, the peptides or the peptide/HLA complexes can be determined according the condition of the subject.

For additional teachings of diagnostic and therapeutic uses of isolated CTLs and peptide/HLA complexes, see, e.g., Thomson et al. (1995) *PNAS* 92: 5845; Altman et al. (1996) *Science* 274: 94–96; Dunbar et al. (1998) *Current Biology* 8: 413–416; Greenberg et al. (1986) *J. Immunol.* 136: 1917; and Kast et al. (1989) *Cell* 59: 603–614.

The present invention is further illustrated by the following examples.

All the publications mentioned in the present disclosure are incorporated herein by reference. The terms and expressions which have been employed in the present disclosure are used as terms of description and not of limitation, and there is no intention in the use of such terms and expressions of excluding any equivalents of the features shown and described or portions thereof, it being recognized that various modifications are possible within the scope of the invention.

TABLE 1

Exemplary Antigens

| Gene | MHC | Peptide | Position | SEQ ID NO: |
|---|---|---|---|---|
| MAGE-1 | HLA-A1 | EADPTGHSY | 161–169 | 1 |
|  | HLA-Cw16 | SAYGEPRKL | 230–238 | 2 |
| MAGE-3 | HLA-A1 | EVDPIGHLY | 168–176 | 3 |
|  | HLA-A2 | FLWGPRALV | 271–279 | 4 |
|  | HLA-B44 | MEVDPIGHLY | 167–176 | 5 |
| BAGE | HLA-Cw16 | AARAVFLAL | 2–10 | 6 |
| GAGE-1,2 | HLA-Cw16 | YRPRPRRY | 9–16 | 7 |
| RAGE | HLA-B7 | SPSSNRIRNT | 11–20 | 8 |
| GnT-V | HLA-A2 | VLPDVFIRC(V) | 2–10/11 | 9 |
| MUM-1 | HLA-B44 | EEKLIVVLF | exon 2/intron | 10 |
|  |  | EEKLSVVLF (wild type) |  | 11 |
| CDK4 | HLA-A2 | ACDPHSGHFV | 23–32 | 12 |
|  |  | ARDPHSGHFV (wild type) |  | 13 |
| β-catenin | HLA-A24 | SYLDSGIHF | 29–37 | 14 |
|  |  | SYLDSGIHS (wild type) |  | 15 |

TABLE 1-continued

Exemplary Antigens

| Gene | MHC | Peptide | Position | SEQ ID NO: |
|---|---|---|---|---|
| Tyrosinase | HLA-A2 | MLLAVLYCL | 1–9 | 16 |
|  | HLA-A2 | YMNGTMSQV | 369–377 | 17 |
|  | HLA-A2 | YMDGTMSQV | 369–377 | 18 |
|  | HLA-A24 | AFLPWHRLF | 206–214 | 19 |
|  | HLA-B44 | SEIWRDIDF | 192–200 | 20 |
|  | HLA-B44 | YEIWRDIDF | 192–200 | 21 |
|  | HLA-DR4 | QNILLSNAPLGPQFP | 56–70 | 22 |
|  | HLA-DR4 | DYSYLQDSPDSFQD | 448–462 | 23 |
| Melan-A$^{MART-1}$ | HLA-A2 | (E)AAGIGILTV | 26/27–35 | 24 |
|  | HLA-A2 | ILTVILGVL | 32–40 | 25 |
| gp100$^{Pme1117}$ | HLA-A2 | KTWGQYWQV | 154–162 | 26 |
|  | HLA-A2 | ITDQVPFSV | 209–217 | 27 |
|  | HLA-A2 | YLEPGPVTA | 280–288 | 28 |
|  | HLA-A2 | LLDGTATLRL | 457–466 | 29 |
|  | HLA-A2 | VLYRYGSFSV | 476–485 | 30 |
| DAGE | HLA-A24 | LYVDSLFFL | 301–309 | 31 |
| MAGE-6 | HLA-Cw16 | KISGGPRISYPL | 292–303 | 32 |

EXAMPLE 1

Generation of Yersinia Expression Vector and Recombinant Yersinia

Strains, Plasmids and Growth Conditions

*Y.enterocolitica* strain E40(pYV40), MRS40(pYV40), which is the isogeneic ampicillin sensitive derivative of E40(pYV40), and their various non-polar mutants (Sory et al. (1995), *Proc. Nat'l Acad. Sci. USA* 92: 11998–12002). Plasmids are listed in Table 1. Bacteria were grown in Brain Heart Infusion (BHI) (Difco, Detroit, Mich.). After overnight preculture, bacteria were diluted 1/20 in fresh BHI, allowed to grow for 30 minutes at room temperature, and synthesis of the Yop virulon was induced by incubation for 150 minutes at 37° C. before infection.

Construction of the Polymutant Yersinia Strains

To construct the yopHOPEM polymutant strain, the yopE, yopH, yopO, yopM and yopP genes were successively knocked out by allelic exchange in the MRS40 strain using the suicide vectors pMRS101 and pKNG101. See, K. Kaniga et al. (1991) "A wide-host range suicide vector for improving reverse genetics in gram-negative bacteria: inactivation of the blaA gene of *Yersinia enterocolitica*" Gene 109: 137–141 and M. R. Sarker et al. (1997) "An improved version of suicide vector pKNG101 for gene replacement in Gram-negative bacteria" *Mol. Microbiol.* 23: 409–411. The various deletions are described in Table 2 in the "suicide vectors and mutators" section. The YopE gene was first mutated using the mutator pPW52 (see, P. Wattiau et al. (1993) "SycE, a chaperone-like protein of *Yersinia enterocolitica* involved in the secretion of YopE" *Mol. Microbiol.* 8: 123–131), giving strain MRS40(pAB4052). Mutation of the YopH gene in this strain with the mutator pAB31 (see, S. D. Mills et al. (1997) "*Yersinia enterocolitica* induces apoptosis in macrophages by a process requiring functional type III secretion and translocation mechanisms and involving YopP, presumably acting as an effector protein" *Proc. Natl. Acad. Sci. USA* 94: 12638–12643) gave the double yopEH mutant MRS40(pAB404). The triple yopEHO mutant MRS40(pAB405) was then obtained by allelic exchange with the mutator pAB34 (see, S. D. Mills et al., 1997). The YopP gene was then mutated with mutator pMSK7 (see S. D. Mills et al. (1997)), leading to the yopEHOP mutant MRS40(pMSK46). The yopHOPEM strain MRS40(pABL403) was finally obtained by allelic exchange with the yopM mutator pAB38 (see, S. D. Mills et al., 1997).

TABLE 2

Plasmids

| Plasmids | Relevant Characteristics | References |
|---|---|---|
| pYV PABL403 | pYV40 yopE$_{21}$, yopHΔ$^{1-352}$ yopOΔ$^{65-558}$, yopP$_{23}$, yopM$_{23}$ Suicide Vectors and mutators | see Example 2 of the present specification |
| pKNG101 | $^{ori}$R6K $^{sac}$BR+ $^{on}$TRK2 $^{sH}$AB+ | K. Kaniga et al. (1991) Gene 109: 137–141. |
| pMRS101 | $^{ori}$R6K $^{sac}$Br+ $^{on}$TRK2 $^{sH}$AB+ $^{ori}$ColE1 $_{bla}$ + | M. R. Sarker and G. R. Cornelis (1997) Mol. Microbiol. 23: 409–411. |
| pAB31 | pMRS101 yopHΔ$_{1-352}$+ | S. D. Mills et al. (1997) Proc. Natl. Acad. Sci. USA 94: 12638–12643. |
| pAB34 | pMRS101 yopOΔ$_{65-558}$+ | S. D. Mills et al. (1997) |
| pAB38 | pMRS101 yopM$_{23}$+ | S. D. Mills et al. (1997) |
| pMSK7 | pMRS101 yopP$_{23}$+ | S. D. Mills et al. (1997) |
| pPW52 | pKNG101 yopE$_{21}$+ | P. Wattiau and G. R. Cornelis (1993) Mol. Microbiol. 8: 123–131. |

Construction of Plasmid YopE$_{130}$-MAGE-1

The sequence encoding protein MAGE-1 was inserted in frame with a sequence encoding a truncated YopE, YopE$_{130}$, containing the first 130 amino acids of YopE. Such a plasmid is graphically depicted in FIG. 1.

The open reading frame of MAGE-1 was amplified by PCR using a MAGE-1 cDNA cloned in pcDNAI/Amp (Invitrogen, Carlsbad, Calif.) as template. The upstream primer, AAACTGCAGATGTCTCTTGAGCAGAGGAGTC (SEQ ID NO:33), consisted of the first nucleotides of the open reading frame of MAGE-1 preceded by a PstI site. The downstream primer, AAACTGCAGTCAGACTCCCTCTTCCTCCTC (SEQ ID NO:34), consisted of nucleotides complementary to the last nucleotides of the open reading frame of MAGE-1 followed by a PstI site. The PCR product was digested with PstI and inserted in frame with the truncated YopE at the PstI site of vector pMS111 (see, Sory et al. (1994) *Molecular Microbiology* 14: 583–594), to yield plasmid YopE$_{130}$-MAGE-1 or pMS111-MAGE-1.

Generation of recombinant Yersinia containing YopE$_{130}$-MAGE-1 pMS111-MAGE-1 (YopE$_{130}$-MAGE-1) was electroporated in bacteria strain DH5αF'IQ. DNA was extracted from some clones and the DNA of a positive recombinant clone was electroporated in bacteria strain SM10. After mobilization of pMS111 from SM10 in Yersinia MRS40 (pABL403), recombinant clones were then selected on agar-containing medium, supplemented with nalidixic acid, sodium-arsenite and chloramphenicol. MRS40 is an isogeneic derivative of E40 sensitive to ampicillin (see, Sory et al. (1995) *Proc. Natl. Acad. Sci. USA* 92: 11998–12002).

Generation of recombinant Yersinia containing YopE$_{130}$-MAGE-4

The sequence encoding protein MAGE-4 was linked in frame to a sequence encoding a truncated YopE, YopE (1–130), containing the first 130 amino acids of YopE. The open reading frame of MAGE-4 was amplified by PCR using a MAGE-4 cDNA cloned in pcDNAI/Amp (Invitrogen) as template. The upstream primer, AAAACT-GCAGATGTCTTCTGAGCAGAAGAGT (SEQ ID NO:35), consisted of the first nucleotides of the open reading frame of MAGE-4 preceded by a PstI site. The downstream primer, AAAAAATCGATTCAGACTCCCTCTTCCTC (SEQ ID NO:36), consisted of nucleotides complementary to the last nucleotides of the open reading frame of MAGE-4 followed by a ClaI site. The PCR was performed for 30 cycles (1 min at 94° C., 2 min at 55° C. and 2 min at 72° C.). The PCR product was digested with PstI and ClaI and inserted in frame with the truncated YopE at the PstI-ClaI sites of vector pMS621. Plasmid pMS621-MAGE-4 was transformed into bacteria strain DH5a F'IQ by electroporation. Positive clones were detected by PCR on bacterial colonies and the DNA of a positive recombinant clone was extracted and transformed into bacteria strain SM10 by electroporation. After mobilization of pMS621-MAGE-4 from SM10 into polymutant Yersinia MRS40 (pABL403), recombinant clones were then selected on agar-containing medium, supplemented with nalidixic acid, sodium m-arsenite and chloramphenicol.

EXAMPLE 2

Targeting EBV-Transformed B Cells with Recombinant Yersinia

One colony of Yersinia MRS40 (pABL403) containing pMS111-MAGE-1 was then grown overnight at 28° C. in LB medium supplemented with nalidixic acid, sodium m-arsenite and chloramphenicol. The overnight culture was diluted in fresh medium in order to obtain an OD (optical density) of 0.2. The fresh culture was amplified at 28° C. for approximately 2 hours. The bacteria were washed in 0.9% NaCl and resuspended at $10^8$ bacteria per ml in 0.9% NaCl. 50,000 EBV-transformed HLA-A1$^+$ B cells (KASOII-EBV) were placed in microwells (96 wells round-bottomed) and pelleted by centrifugation. The supernatant was discarded and various dilutions of bacteria were added in 100 μl of complete RPMI 1640 (culture media was supplemented with 10% FCS and with L-arginine (116 mg/ml), L-asparagine (36 mg/ml), L-glutamine (216 mg/ml). Two hours after infection, gentamicin (30 μg/ml) was added for the next two hours, and the cells were finally washed three times.

As a negative control, the same cells were also infected with Yersinia MRS40 (pABL403) containing pMS621, a plasmid which encodes only the truncated YopE, i.e., YopE$_{130}$.

Figure 2A:
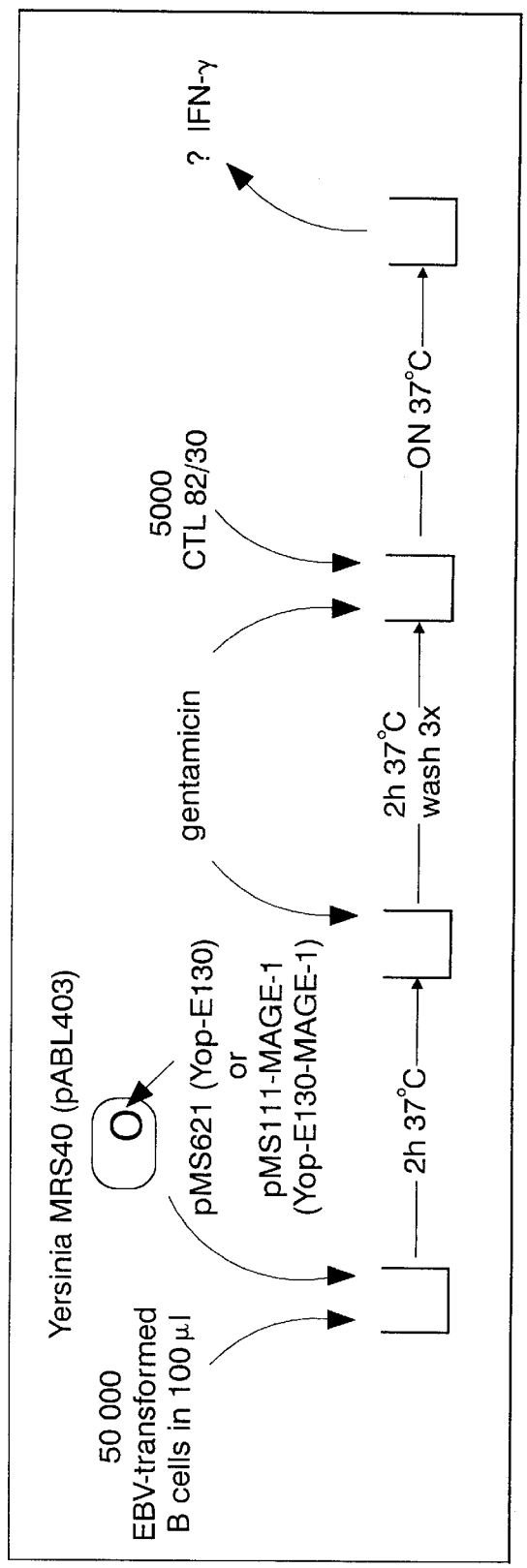
FIG. 2 (A) depicts the procedure for stimulating CTL 82/30 with EBV-transformed human B cells (HLA-A1) mixed with recombinant Yersinia; (B) depicts the quantitation of IFN-released by activated CTLs.

EBV-B Cells infected with the recombinant Yersinia-MAGE1 were recognized by MZ2-CTL 82/30. MZ2-CTL 82/30 are specific for the MAGE-1 peptide EADPTGHSY which is presented by HLA-A1 (U.S. Pat. No. 5,342,774). 5000 MZ2-CTL 82/30 cells were added in each microwell containing the Yersinia in a final volume of 100 μl of Iscove's complete medium (culture medium was supplemented with 10% human serum, L-arginine (116 mg/ml), L-asparagine (36 mg/ml), L-glutamine (216 mg/ml), strep-tomycine (0.1 mg/ml), penicillin (200 U/ml), IL-2 (25 U/ml) and gentamicin (15 μg/ml). After overnight incubation, the presence of IFN-gamma (that is produced by CTL upon activation) in the supernatant of the co-culture was tested in a standard ELISA assay (Biosource, Fleurus, Belgium). FIG. 2A graphically depicts such a procedure.

Figure 2B:
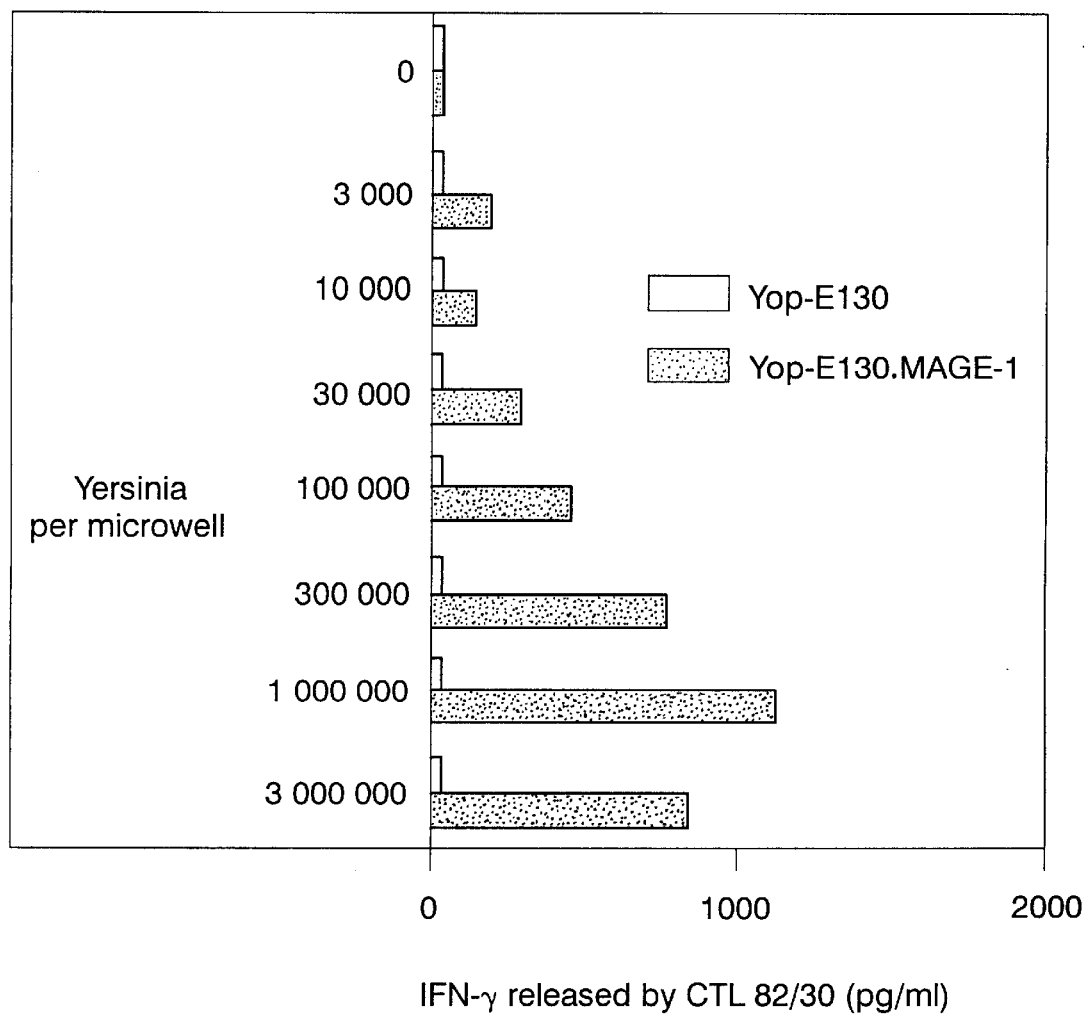

As indicated in FIG. 2B, the HLA-A1$^+$ B cells infected with Yersinia encoding YopE$_{130}$-MAGE-1 were recognized by the CTL 82/30, while the same cells infected with the control plasmid YopE$_{130}$ were not. The optimal concentration of bacteria is around 1,000,000 per microwell.

EXAMPLE 3

Generation of Recombinant Vaccinia WR Viruses

Parental WR strain of Vaccinia (vP1170) contained the parent vector pKILGPT of 2826 bp (Virogenetics, Troy, N.Y.). A sequence coding for MAGE-1, placed after the Vaccinia Virus H6 promoter, was cloned into the pKILGPT vector, creating donor plasmid MAW035. A similar MAGE-4a donor plasmid vector was constructed by replacing the MAGE-1 cDNA with the MAGE-4a cDNA.

The donor plasmids was transfected into CEF cells containing the genomic DNA of vaccinia strain WR, yielding recombinant vaccinia viruses WR-MAGE-1 and WR-MAGE-4, respectively, by way of in vivo recombination. The procedure can be found in, e.g., Perkins et al. (1989) *J. Virol.* 63: 3829–3936.

EXAMPLE 4

Generation of Recombinant ALVAC-MAGE-1 Viruses

A MAGE-1 coding sequence, placed after the Vaccinia Virus H6 promoter, was cloned into the pUC8-based vector to generate donor plasmid MAW036.

Recombinant ALVAC-MAGE-1 virus was generated by using the donor plasmid MAW036 by following well known procedures, e.g., as described in *Current Protocols* in *Molecular Cloning* (Ausubel et al., John Wiley & Sons, New York).

EXAMPLE 5

Generation of Recombinant Adenoviruses

For the construction of the recombinant adenovirus Ad-MAGE-4, the plasmid pAd-CMVIcpA-MAGE-4 (containing the MAGE-4 cDNA under the control of the CMV promoter) was obtained by inserting into the NotI site of vector pAd-CMVIcpA (provided by Celia GARCIA and Thierry RAGOT, URA CNRS 1301), the MAGE-4a complete cDNA.

The recombinant adenovirus Ad-MAGE-4 was constructed by in vivo homologous recombination in cell line 293 between pAd-CMVIcpA-MAGE-4 and Ad-βgal genomic DNA. Briefly, 293 cells were cotransfected with 5 µg of plasmid pAd-CMVIcpA-MAGE-4 linearized with XmnI and 5 µg of the large ClaI fragment of Adeno-βgal DNA (Stratford-Perricaudet et al. (1992), *J. Clin. Invest.*, 90: 626–630 and Patent FR 9603207. The recombinant adenovirus was plaque purified and the presence of the transgene was assessed by restriction analysis of the adenoviral DNA. Recombinant adenoviruses were propagated in 293 cells and purified by double cesium chloride density centrifugation. The viral stocks were stored in aliquots with 10% glycerol in liquid nitrogen and titered by plaque assay using 293 cells.

EXAMPLE 6

General Methods and Procedure for Isolation of CTL Clones

Processing of Human Blood

Peripheral blood was obtained from the local blood bank (non cancer patient) as standard buffy coat preparations. Peripheral blood mononuclear cells (PBMC) were isolated by centrifugation on Lymphoprep (Nycomed Pharma, Oslo, Norway). In order to minimize contamination of PBMC by platelets, the preparation was first centrifuged for 20 min at 1000 rpm at room temperature. After removal of the top 20–25 ml containing most of the platelets, the tubes were centrifuged for 20 min at 1500 rpm at room temperature. PBMC were depleted of T cells by rosetting with 2-aminoethylisothiouronium (Sigma) treated sheep erythocytes. Rosetted T cells were treated with $NH_4Cl$ (160 mM) to lyse the sheep erythrocytes and washed. The $CD8^+$ T lymphocytes were isolated by positive selection using an anti-CD8 monoclonal antibody coupled to magnetic microbeads (Miltenyi Biotech, Germany) and by sorting through a magnet. The $CD8^+$ T lymphocytes were frozen and thawed the day before the start of the primary culture and cultured overnight in Iscove's medium containing L-asparagine (0.24 mM), L-arginine (0.55 mM), L-glutamine (1.5 mM), 10% human serum (hereafter referred to as complete Iscove's medium) and supplemented with 2.5 U/ml IL-2.

The lymphocyte-depleted PBMC were frozen or used immediately for dendritic cell cultures. Cells were left to adhere for 1–2 hrs at 37° C. in culture flasks (Falcon) at a density of $2 \times 10^6$ cells/ml in RPMI 1640 medium supplemented with L-asparagine (0.24 mM), L-arginine (0.55 mM), L-glutamine (1.5 mM) and 10% fetal calf serum (complete medium). Non-adherent cells were discarded and adherent cells were cultured in the presence of IL-4 (100 U/ml) and GM-CSF (100 ng/ml) in complete medium. Cultures were fed on day 2 and/or day 4 by removing ⅓ of the volume of the medium and adding fresh medium with IL-4 (100 U/ml) and GM-CSF (100 ng/ml). For experiments in Examples 7 and 8, on day 6 or 7, the non-adherent cell population was used as a source of enriched dendritic cells. For experiments in Example 9, cultures were frozen on day 4, and on the day before each stimulation, dendritic cells were thawed and grown overnight in complete medium supplemented with 100 U/ml IL-4 and 100 ng/ml GM-CSF. Epstein Barr Virus (EBV) immortalized B cells (hereafter referred as to EBV-B cells) were obtained following the standard protocol.

Cytokines

Human recombinant IL-2 was provided by Biogen (Geneva, Switzerland) or purchased from Chiron BV, Amsterdam. Human recombinant IL-4, IL-6 and IL-12 were obtained by the present inventors. Human recombinant IL-7 was purchased from Genzyme (Cambridge, Mass.). Human recombinant GM-CSF was purchased from Sandoz (Leucomax, Sandoz Pharma, Basel, Switzerland).

Interferon γ production assay.

5000 target cells were cultured overnight with 2000 CTL in 100 µl per well complete Iscove's medium supplemented with 25 U/ml IL-2 in 96 well round bottom plates. The production of interferon γ (IFN-γ) was measured in 50 µl supernatant by ELISA (Biosource).

Procedure for isolating CTL clones $CD8^+$ T lymphocytes from an individual without cancer were stimulated in microwells with autologous monocyte-derived dendritic cells infected with a recombinant ALVAC canarypoxvirus encoding MAGE-1 or a recombinant adenovirus encoding MAGE-4. After several rounds of stimulation, an aliquot of each microculture was tested for specific lysis of autologous targets infected with a recombinant Vaccinia encoding MAGE-1 or MAGE-4. The positive microcultures were cloned by limiting dilution, using autologous stimulator cells infected with a recombinant Yersinia encoding MAGE-1 or MAGE-4. The clones were tested for specific lysis of autologous targets infected with a recombinant Vaccinia encoding MAGE-1 or MAGE-4. Positive clones were obtained. The antigenic peptides and the HLA presenting molecules were identified.

Examples 7–9 describe the isolation of three CTL clones and the identification of the respective antigenic peptides specifically recognized by such CTL clones.

EXAMPLE 7

A Mage-1 Derived Peptide Presented by HLA-Cw3 Molecules to Cytolytic T Lymphocytes Isolation of MAGE-1 specific CTL clone 462/F3.2

Autologous dendritic cells from donor LB 1137 (HLA-A2 A3 B4402 B60 Cw3 Cw5) were infected with the ALVAC-MAGE-1 at a multiplicity of infection of 30 in RPMI containing 10% FCS at 37° C. under 5% $CO_2$. After 2 hours, the infected dendritic cells were washed. For in vitro stimulation, 150,000 $CD8^+$ T lymphocytes and 30,000 infected dendritic cells were cocultured in microwells in 200 μl Iscove's medium containing L-asparagine (0.24 mM), L-arginine (0.55 mM), L-glutamine (1.5 mM), 10% human serum (hereafter referred to as complete Iscove's medium) and supplemented with IL-6 (1000 U/ml) and IL-12 (10 ng/ml). The $CD8^+$ lymphocytes were weekly restimulated with autologous dendritic cells freshly infected with the ALVAC-MAGE-1 and grown in complete Iscove's medium supplemented with IL-2 (10 U/ml) and IL-7 (5 ng/ml).

After several rounds of stimulation, an aliquot of each microculture was tested for specific lysis of autologous target cells. Autologous EBV-B cells were infected for two hours with either the parental vaccinia WR (batch LVAR) or the WR-MAGE-1 construct (vP 1267), using a multiplicity of infection of 20, and labeled with $Na(^{51}Cr)\ O_4$. Afterwards, EBV-B cells (target cells) were washed, and added to the responder cells at an effector to target ratio of approximately 40:1. Unlabeled K562 cells were also added ($5\times10^4$ per V-bottomed microwell) to block natural killer activity. Chromium release was measured after incubation at 37° C. for 4 hours. The individual microcultures were tested in duplicate on each target.

Figure 3A:
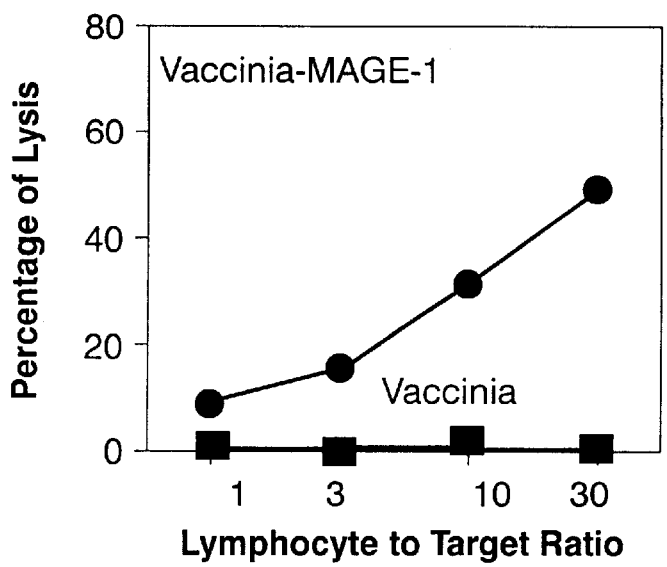
FIGS. 3A–3D depict the specific recognition by CTL clone 462/F3.2 of a MAGE-1 antigenic peptide presented by HLA-Cw3.

The positive microcultures were cloned by limiting dilution, using autologous EBV-B cells infected with recombinant Yersinia expressing the $YopE_{130}$-MAGE-1 protein as stimulating cells, and allogeneic EBV-B cells (LG2-EBV) as feeder cells. The cultures were restimulated similarly on day 7, and clones were maintained in culture by weekly restimulation with allogeneic EBV-B cells (LG2-EBV) in complete Iscove's medium supplemented with 0.5 μg/ml PHA-HA16 (Murex) and 50 U/ml of IL-2. At day 3 after restimulation, the clones were washed to remove the PHA-HA16 in the culture medium. The clones were tested for specific lysis of autologous EBV-B cells infected with the vaccinia-MAGE-1 construct. Clone 462/F3.2 was found positive (FIG. 3a) and used in subsequent experiments.

The MAGE-1 Epitope is Presented to CTL by HLA-Cw3 Molecules

As donor LB 1137 expresses a number of different HLA molecules as described supra, each HLA was tested to determine which one presented the antigen recognized by CTL 462/F3.2.

The HLA-A*0201 coding sequence was obtained from a cDNA library of cell line BB49, cloned into expression vector pcDNAI/Amp. The HLA-A3 coding sequence was isolated from a cDNA library of cell line LB33 cloned into expression vector pcDNA3. The HLA-B*4402 coding sequence was isolated by RT-PCR from cell line LB33 and cloned in expression vector pcDNAI/Amp. The HLA-B*40012 (B60) coding sequence was derived by RT-PCR from cell line HA7-RCC and cloned in expression vector pcDNA3. The HLA-Cw3 coding sequence was cloned in expression vector pCR3. The HLA-Cw5 was isolated from cell line LB373 by RT-PCR and cloned into pcDNA3. RT-PCR reactions were performed on RNA of EBV-transformed B cells as template. The PCR products were cloned into expression vector pcDNA3 (Invitrogen B, the Netherlands). DNA was extracted from recombinant clones and sequenced partially on the sense and partially on the antisense strand by the dideoxy-chain termination method (Thermosequenase™ cycle sequencing kit, Amersham).

Figure 3B:
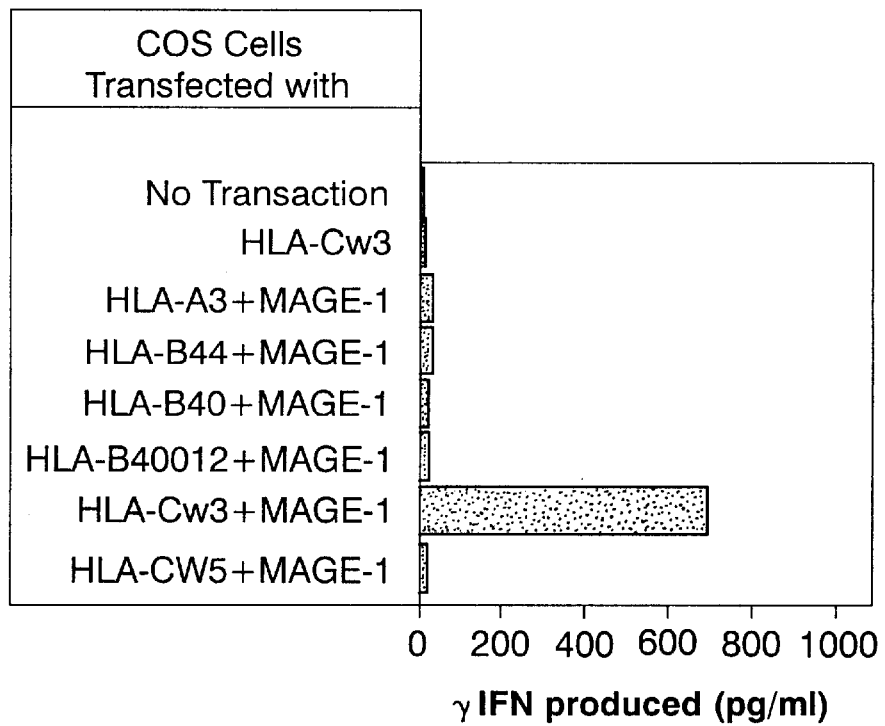

COS cells were transfected with plasmids encoding one of the six HLA-class I molecules together with the cDNA of MAGE-1. In brief, $1.5\times10^4$ COS cells distributed in microwells were cotransfected with 50 ng of plasmid pcDNAI containing the MAGE-1 cDNA and 50 ng of plasmid pcDNA3 containing the cDNA coding for one of the six HLA-class I molecules that were expressed by donor LB1137, using 1 μl of Lipofectamine reagent (Gibco BRL). The COS cells were incubated 5 hours at 37° C. and 8% $CO_2$ in the transfection mixture and 200 μl of culture medium was added. After overnight culture, transfectants were tested for their ability to stimulate the production of IFN-γ by clone 462/F3.2. Briefly, 1500 CTLs were added to each microwell 2OW containing transfected cells, in a final volume of 100 μl of Iscove's complete medium containing 25 U/ml of IL-2. After 24 hours, 50 μl supernatant was tested for its IFN-γ content in a WEHI bioassay which measured the cytotoxic effect of IFN-γ on cells of WEHI-164 clone 13 in a MTT colorimetric assay. Only those cells transfected with both HLA-Cw3 and MAGE-1 stimulated CTL clone 462/F3.2 to produce IFN-γ (FIG. 3b). COS cells transfected with MAGE-1 or HLA-Cw3 alone did not stimulate the CTL clone.

Antigenic Peptides and CTL Assay.

In order to identify the MAGE-1 peptide recognized by clone 462/F3.2, peptides (16 amino-acids) corresponding to parts of the MAGE-1 protein were synthesized, loaded on the autologous EBV-B cells and tested for recognition. Peptides were synthesized on solid phase using F-moc for transient $NH_2$-terminal protection. Lyophilized peptides were dissolved at 20 mg/ml in DMSO, diluted at 2 mg/ml in 10 mM acetic acid and stored at −20° C.

Peptides were tested in chromium release assays in which 1000 $^{51}$Cr-labeled target cells were incubated with 10 μg/ml of peptide in 96-well microplates (100 μl/well) for 20 min at room temperature, prior to adding 100 μl medium containing 10,000 CTL. The assay was terminated after 4 hours of incubation at 37° C. and 8% CO2.

Figure 3C:
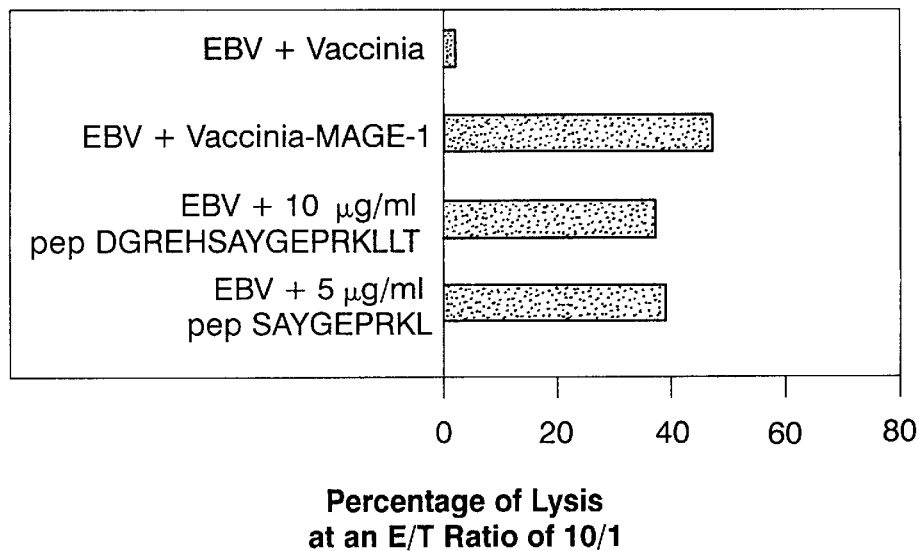

Autologous EBV-B cells incubated with peptide DGREHSAYGEPRKLLT (MAGE-1 (SEQ ID NO:37) $_{225-240}$) were recognized by CTL 462/F3.2 (FIG. 3c). This long peptide contained a 9-amino-acid peptide SAYGEPRKL (MAGE-1 $_{230-238}$) (SEQ ID NO:2) which contained adequate anchor residues for HLA-Cw3: a Y in position 3 and a L at the C-terminus. DGREHSAYGEPRKLLT (SEQ ID NO:37) was screened for prediction of an HLA-Cw3 binding peptide with the software available at "http://bimas.dcrt.nih.gov/molbio/hla_bind /index.html". Peptide SAYGEPRKL (MAGE-1 $_{230-238}$) (SEQ ID NO:2) had the highest score for binding to HLA-Cw3. It was recognized by CTL462/F3.2 in a cytotoxicity assay at an effector to target ratio of 10:1 (FIG. 3c).

Recognition by CTL Clone 462/F3.2 of HLA-Cw3 Positive Tumor Cells Expressing MAGE-1

Figure 3D:
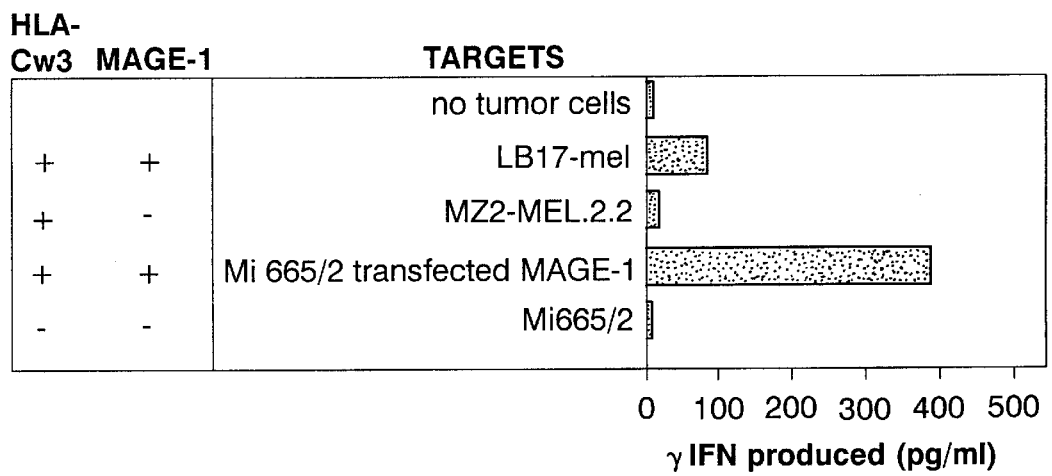

The activation of CTL 462/F3.2 by tumor cell lines that express HLA-Cw3 and MAGE-1 was tested in an IFN-γ production assay. CTL clone 462/F3.2 recognized the HLA-Cw3 positive tumor cell line LB17-MEL which expresses MAGE-1 (FIG. 3d). The melanoma cell line Mi 665/2 E+ clone 2, that was transfected with a genomic fragment containing the open reading frame of MAGE-1 (as described in U.S. Pat. NO. 5,342,774), was also recognized by clone 462/F3.2, whereas the parental cell line Mi 665/2 was not recognized.

EXAMPLE 8

A MAGE-1 Derived Peptide Presented by HLA-B5301 Molecules to Cytolytic T Lymphocytes
Isolation of MAGE-1 Specific CTL Clone 456/H7.11

Autologous dendritic cells from donor LB1801 (HLA-A201, A28, B4401, B5301, Cw04, Cw0501) were infected with the ALVAC-MAGE-1 construct at a multiplicity of infection of 30 in RPMI containing 10% FCS at 37° C. under 5% $CO_2$. After 2 hours, the infected dendritic cells were washed twice. For in vitro stimulation, 150,000 CD8+ lymphocytes and 30,000 infected dendritic cells were cocultured in round bottomed microwells in 200 microliters Iscove's medium containing L-asparagine (0.24 mM), L-arginine (0.55 mM), L-glutamine (1.5 mM), 10% human serum (hereafter referred as complete Iscove's medium) and supplemented with IL-6 (1000 U/ml) and IL12 (10 ng/ml). The CD8+ lymphocytes were weekly restimulated with autologous dendritic cells freshly infected with the ALVAC-MAGE-1 construct and grown in complete Iscove's medium supplemented with IL-2 (10 U/ml) and IL-7 (5 ng/ml).

Autologous EBV-B cells were infected for 2 hours with either the parental vaccinia WR (vP1170) or the recombinant vaccinia WR-MAGE-1 (vP1188) using a multiplicity of infection of 20, and labeled with $Na(^{51}Cr)O_4$. Target cells were washed, and added to the responder cells at an effector to target ratio of approximately 40:1. Unlabeled K562 were also added ($5\times10^4$ per V-bottomed microwell) to block natural killer activity. Chromium release was measured after incubation at 37° C. for 4 hours. The individual microcultures were tested in duplicate on each target.

Figure 4A:
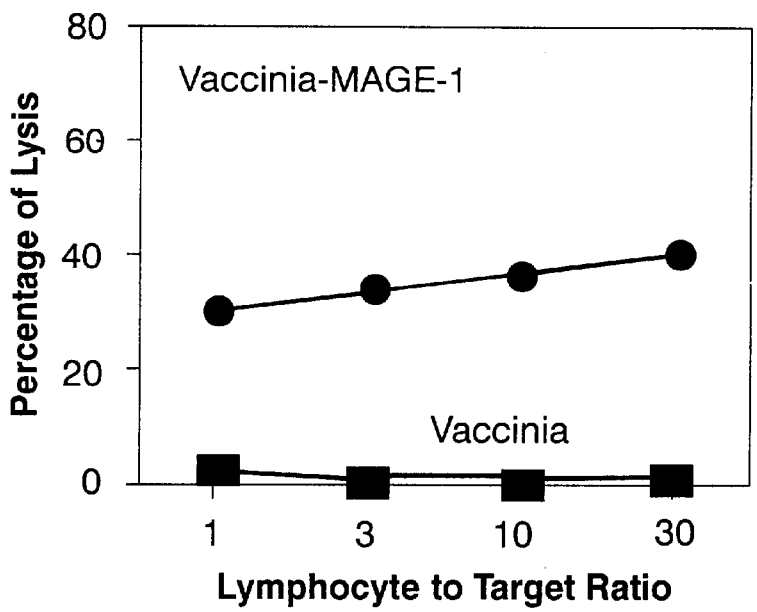

The microcultures containing cells that specifically lysed autologous EBV-B cells infected with the vaccinia-MAGE-1 construct were cloned by limiting dilution using autologous EBV-B cells previously infected with the Yersinia expressing $YopE_{1-130}$-MAGE-1 as stimulating cells, and allogeneic EBV-B cells (LG2-EBV) as feeder cells. CTL clones were maintained in culture by weekly restimulation in complete Iscove's medium supplemented with 50 U/ml of IL2. The clones were tested for specific lysis of autologous EBV-B cells infected with the vaccinia-MAGE-1 construct. Clone 456/H7.11 was found positive (FIG. 4a) and used in the following experiments. The CTL was restimulated weekly with LG2-EBV as feeder cells and alternately, purified phytohaemagglutin (PHA-HA16; MUREX) (0.5 mg/ml) or autologous EBV-B cells previously infected with the Yersinia-$YopE_{1-130}$-MAGE-1.

Antigenic Peptides and CTL Assay

In order to identify the MAGE-1 peptide recognized by clone 456/H7.11, peptides (16 amino-acids) corresponding to parts of the MAGE-1 protein were synthesized, loaded on the autologous EBV-B cells and tested for recognition. Peptides were synthesized on solid phase using F-moc for transient NH2-terminal protection. Lyophilized peptides were dissolved at 20 mg/ml in DMSO, diluted at 2 mg/ml in 10 mM acetic acid and stored at −20° C. Peptides were tested in chromium release assay where 1 000 $^{51}$Cr-labeled target cells were incubated for 15 min at room temperature in V-bottomed microplates with 5 µg/ml of peptide, before adding an equal volume containing 5,000 CTLs. The assay was terminated after 4 hours of incubation at 37° C. and 8% CO2. Peptides QVPDSDPARYEFLWGP (MAGE-1 253–268) (SEQ ID NO:38) and SDPARYEFLWGPRALA (MAGE-1 257–272) (SEQ ID NO:39) scored positive.

Identification of the HLA Presenting Molecule

To know which HLA molecule presented both 16-mers peptides to CTL clone 456/H7.11, peptides were tested in a chromium release assay using, as target cells, EBV-B cells from different donors that shared HLA molecules with donor LB1801. Clone 456/H7.11 were able to recognize the peptide only when presented by autologous cells (Table 3). Because, no EBV-B cells expressing the HLA-B5301 molecule was tested, the cDNA coding for HLA-B5301 of donor LB1801 was isolated.

The HLA-B5301 coding sequence was amplified by RT-PCR using RNA of LB1801-EBV-transformed B cells as template. The PCR products were cloned into expression vector pcDNA3 (Invitrogen BV, the Netherlands). DNA was extracted from recombinant clones and sequenced partially on the sense and partially on the antisense strand to check that it was a sequence encoding HLA-B5301. The sequence for HLA-B5301 is described by Mason and Pasham (1998), Tissue Antigens 51: 417–466.

TABLE 3

| Target Cells | HLA Typing | | | | % of Lysis | |
| --- | --- | --- | --- | --- | --- | --- |
| | | | | | No Peptide | SDPARYEFLWGPRALA |
| LB1801 (autologous) | A2 A28 | B4402 B53 | CwD4 Cw0501 | | 5 | 41 |
| LB1118 | A2 A3 | B8 B61 | Cw2 Cw7 | | 19 | 15 |
| LB33 | A24 A28 | B13 B4402 | Cw6 Cw7 | | 22 | 18 |
| LB1158 | A2 A3 | B35 B51 | Cw1 Cw4 | | 6 | 4 |
| LB1137 | A2 A3 | B4402 B60 | Cw3 Cw5 | | 5 | 3 |
| LG2 | A24 A32 | B3503 B4403 | Cw4 | | 1 | 4 |
| LB1819 | A2 | B44 B57 | Cw5 Cw7 | | 0 | 4 |
| LB1161 | A3 A26 | B39 B4402 | | | 1 | 8 |
| LB1213 | A24 | B18 B35 | Cw4 Cw7 | | 0 | 4 |

Table 3: Lysis by CTL 456/H7.11 of various EBV-B cells (target cells) pulsed with MAGE-1 peptide. EBV-B cells were 51Cr labeled and incubated with CTL at an effector to target cell ratio of 5/1 in the presence (or not) of 5 microgrammes of peptide SDPARYEFLWGPRALA. Chromium release was measured after 4 hours.

Figure 4B:
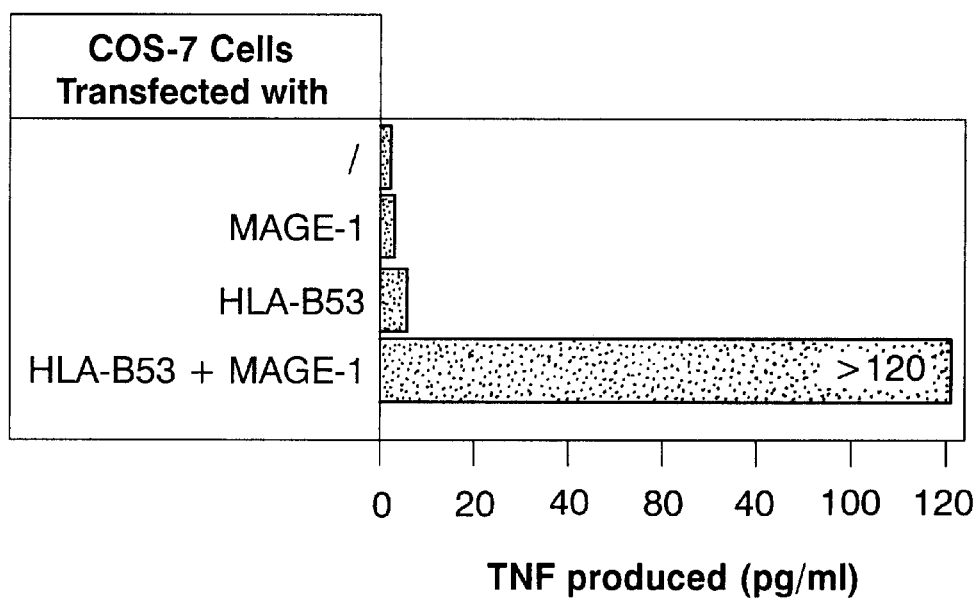

COS-7 cells were transfected with plasmids encoding HLA-B5301 molecule together with MAGE-1 cDNA. In brief, $1.5\times10^4$ COS-7 cells distributed in microwells were cotransfected with 100 ng of plasmid pcDNAI containing the MAGE-1 cDNA, 100 ng of plasmid pcDNA3 containing the cDNA coding for HLA-B5301 molecule of donor LB 1801, and one microliter of lipofectamine (Gibco BRL). The COS-7 cells were incubated 24 hours at 37° C. and 8% $CO_2$. These transfectants were then tested for their ability to stimulate the production of TNF by clone 456/H7.11. Briefly, 1,500 CTLS were added to the microwells containing the transfectants, in a total volume of 100 ml of Iscove's complete medium containing 25 U/ml of IL-2. After 24 hours, the supernatant was collected and its TNF content was determined by testing its cytotoxic effect on cells of WEHI-164 clone 13 in a standard MTT colorimetric assay. The cells transfected with both HLA-B53 and MAGE-1 stimulated CTL clone 456/H7.11 to produce TNF (FIG. 4b). COS-7 cells transfected with MAGE-1 or HLA-B53 alone did not stimulate the CTL clone.

Identification of the Antigenic Peptide

Figure 4C:
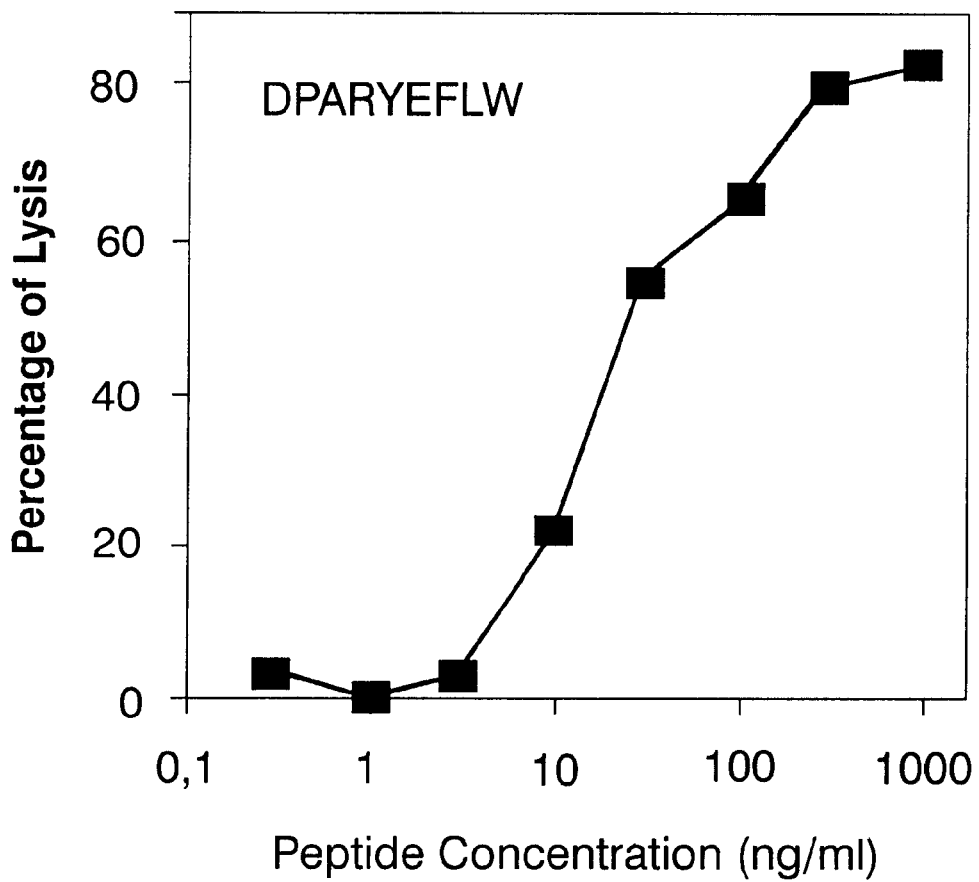

To identify the sequence of the shortest synthetic peptide recognized by clone 456/H7.11, we compared the lysis by the CTL of autologous EBV-B cells, loaded with the MAGE-1 peptide SDPARYEFLWGPRALA (MAGE-1 257–272) (SEQ ID NO:39) or the MAGE-4 peptide GSN-PARYEFLWGPRAL (MAGE-4 264–279) (SEQ ID NO:40), in a chromium release at an effector target ratio of 10 and a final concentration of peptide of 5 µg/ml. The MAGE-1 peptide, but not the MAGE-4 peptide, was recognized. The 10-mer peptide SDPARYEFLW and the 9-mer peptide DPARYEFLW were then synthesized and tested in a cytotoxic assay at an effector to target ratio of 5. Both peptides were recognized. The shorter peptide was then tested at different concentration at an effector to target ratio of 10 (FIG. 4c). Half-maximal lysis was obtained at between 10 and 100 ng/ml.

EXAMPLE 9

A MAGE-4 Derived Peptide Presented by HLA-A2 Molecules to Cytolytic T Lymphocytes Isolation of MAGE-4 Specific CTL Clone H4/13

Autologous dendritic cells from donor LB 1137 (HLA-A2, -A3, -B4402, -B60, -Cw3, -Cw5) were infected with the Ad-MAGE-4 construct at a multiplicity of infection of 200 in RPMI containing 10% FCS at 37° C. under 5% $CO_2$. After 2 hours, the infected dendritic cells were washed. For in vitro stimulation, 150,000 $CD8^+$ T lymphocytes and 30,000 infected dendritic cells were cocultured in microwells in 200 µl Iscove's medium containing L-asparagine (0.24 mM), L-arginine (0.55 mM), L-glutamine (1.5 mM), 10% human serum (hereafter referred to as complete Iscove's medium) and supplemented with IL-6 (1000 U/ml) and IL-12 (10 ng/ml). The $CD8^+$ lymphocytes were weekly restimulated with autologous dendritic cells freshly infected with the Ad-MAGE-4 construct and grown in complete Iscove's medium supplemented with IL-2 (10 U/ml) and IL-7 (5 ng/ml) These cells were tested as responder cells in the following assay.

Autologous EBV-B cells were infected for 2 hours with either the parental vaccinia WR parent (batch vP1170 or batch L VAR) or the recombinant vaccinia WR-MAGE-4 (batch vP1545) using a multiplicity of infection of 20, and labeled with $Na(^{51}Cr)O_4$. These target cells were washed, and added to the responder cells at an effector to target ratio of approximately 40:1. Unlabeled K562 cells were also added ($5\times10^4$ per V-bottomed microwell) to block natural killer activity. Chromium release was measured after incubation at 37° C. for 4 hours. The individual microcultures were tested in duplicate on each target.

Figure 5A:
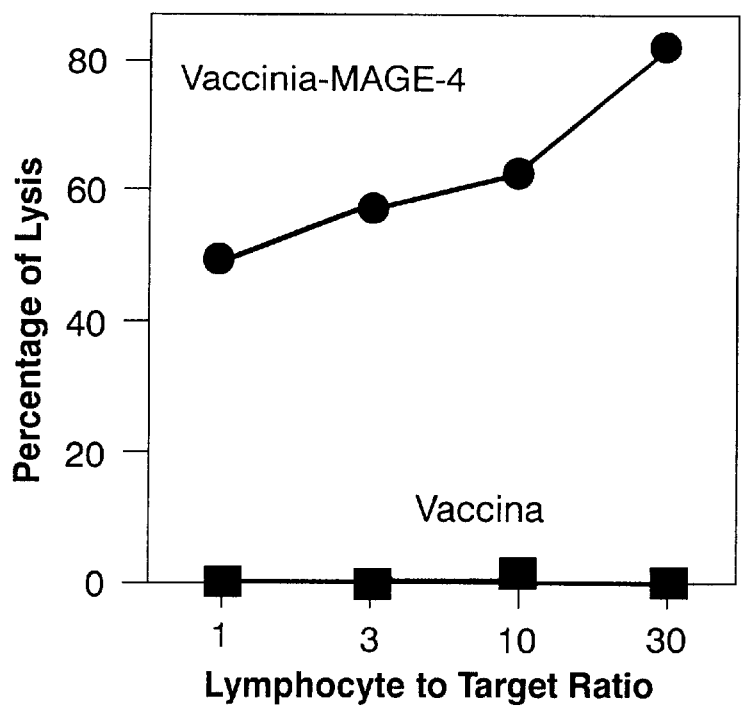

The microcultures containing cells that specifically lysed autologous EBV-B cells infected with the vaccinia-MAGE-4 construct were cloned by limiting dilution using, as stimulating cells, autologous EBV-B cells infected with the recombinant Yersinia expressing $YopE_{1-130}$-MAGE-4 (described above), and using allogeneic EBV-B cells (LG2-EBV) as feeder cells. Infection of EBV-B cells with Yersinia $YopE_{1-130}$-MAGE-4 was done as follows: one colony of Yersinia MRS40 (pABL403) containing pMS621-MAGE-4 ($YopE_{1-130}$-MAGE-4) was grown overnight at 28° C. in LB medium supplemented with nalidixic acid, sodium m-arsenite and chloramphenicol. From this culture, a fresh culture at an OD (600 nm) of 0.2 was then amplified at 28° C. for approximately 2 hours. The bacteria were then washed in 0.9% NaCl and resuspended at $10^8$ bacteria per ml in 0.9% NaCl. Irradiated EBV-B cells were infected at a multiplicity of infection of 20 in complete RPMI 1640 (culture media was supplemented with 10% FCS, and with L-arginine (116 mg/ml), L-asparagine (36 mg/ml), L-glutamine (216 mg/ml). Two hours after infection, gentamycin (30 µg/ml) was added for the next two hours, and the cells were finally washed 3 times. CTL clones were maintained in culture by weekly restimulation with either Yersinia $YopE_{1-130}$-MAGE-4 infected EBV-B cells, HLA-A2 melanoma cell line QUAR (LB1751-MEL) that expressed MAGE-4 , or PHA (0.5 µg/ml) in complete Iscove's medium supplemented with 50 U/ml of IL-2. The clones were tested for specific lysis of autologous EBV-B cells infected with the vaccinia-MAGE-4 construct. Clone H4/13 was found positive (FIG. 5a) and used in the following experiments.

The MAGE-4 Epitope is Presented to CTL by HLA-A2 Molecules

The lysis by CTL clone H4/13 of EBV-B cells infected with the vaccinia-MAGE-4 construct was inhibited by addition of an anti-HLA-A2 monoclonal antibody but not by addition of an anti-HLA-A3 or an anti-HLA-B,C monoclonal antibody. This indicated that the MAGE-4 epitope was presented by HLA-A2 molecules.

Figure 5B:
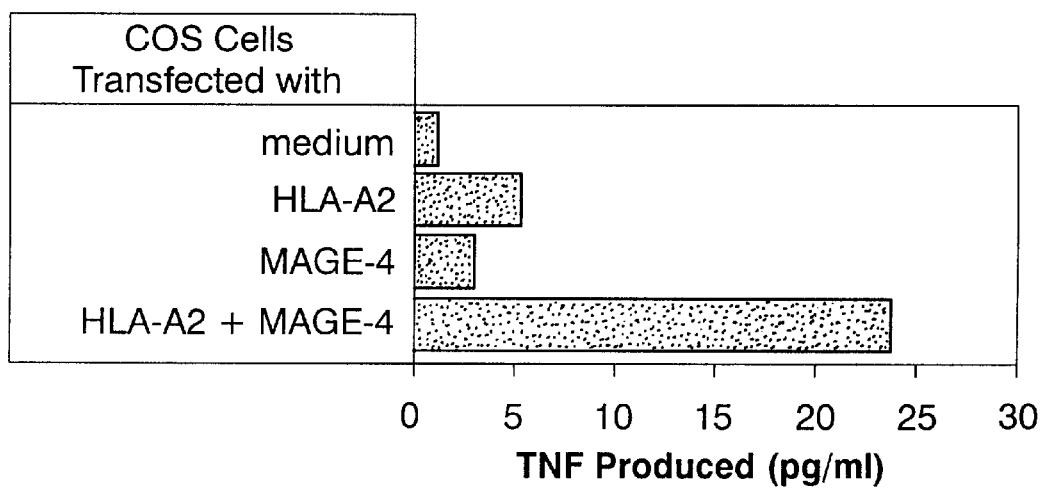

Cos cells were transfected with plasmids encoding the HLA-A2 molecule together with the cDNA of MAGE-4. In brief, $1.5\times10^4$ Cos cells distributed in microwells were cotransfected with 50 ng of plasmid pcDNAI containing the MAGE-4 cDNA, 50 ng of plasmid pcDNAI/Amp containing the genomic DNA coding for the HLA-A2 molecule and 1 µl of DMRIEC (Gibco BRL). The Cos cells were incubated 24 hours at 37° C. and 8% $CO_2$. These transfectants were then tested for their ability to stimulate the production of TNF by clone H4/13. Briefly, 2000 CTL were added to the microwells containing the transfectants, in a total volume of 100 µl of Iscove's complete medium containing 25 U/ml of IL-2. After 24 hours, the supernatant was collected and its TNF content was determined by testing its cytotoxic effect on cells of WEHI-164 clone 13 in a standard MTT colorimetric assay. The cells transfected with both HLA-A2 and MAGE-4 stimulated CTL clone H4/13 to produce TNF (FIG. 5b). Cos cells transfected with MAGE-4 or HLA-A2 alone did not stimulate the CTL clone.

Determination of the Antigenic Peptide

In order to identify the MAGE-4 peptide recognized by clone H4/13, PCR reactions were performed using the MAGE-4 cDNA as template, an upstream primer (S) consisting of the first nucleotides of the open reading frame of MAGE-4 and 8 downstream primers (AS1 to AS8) (FIG. 6), separated from each other by approximately 100–120 bp in the open reading frame of MAGE-4. The PCR was performed for 30 cycles (1 min at 94° C., 2 min at 63° C. and 3 min at 72° C. This led to the amplification of 8 fragments of MAGE-4 of different lengths (MAGE-4(1) to MAGE-4 (8)), the longer one (MAGE-4(1)) containing the entire open reading frame of MAGE-4. PCR products were ligated into the pcDNA3.1/V5/His-TOPO vector and the recombinant vectors were transformed into E. coli cells (Topo TA cloning kit, Invitrogen). Colonies were analyzed by PCR and DNA of positive clones was extracted and used to transfect HeLa cells together with a plasmid encoding the HLA-A2 molecule. Briefly, $2 \times 10^4$ HeLa cells distributed in microwells were cotransfected with 50 ng of plasmid pcDNA3.1/V5/His-TOPO containing the MAGE-4 fragment, 50 ng of plasmid pcDNA1/Amp containing the genomic DNA coding for the HLA-A2 molecule and 1 μl of Lipofectamine (Gibco BRL). The HeLa cells were incubated 24 hours at 37° C. and 8% $CO_2$. These transfectants were then tested for their ability to stimulate the production of TNF by clone H4/13 as described above. Transfection with inserts S-AS1 and S-AS2 were positive, transfections with the other constructs were negative. This led to the identification of a MAGE-4 fragment of 130 bp,
TGATGGGAGGGAGCACACTGTCTATGGG-GAGCCCAGGAAACTGCTCACCCAAGAT-TGGGTGCAGGAAAACTACCTGGAGTAC-CGGCAGGTACCCGGCAGTAATCCTGCGCGCTAT GAGTTCCTGTGGGGT (SEQ ID NO:43), encoding the epitope recognized by clone H4/13.

Figure 5C:
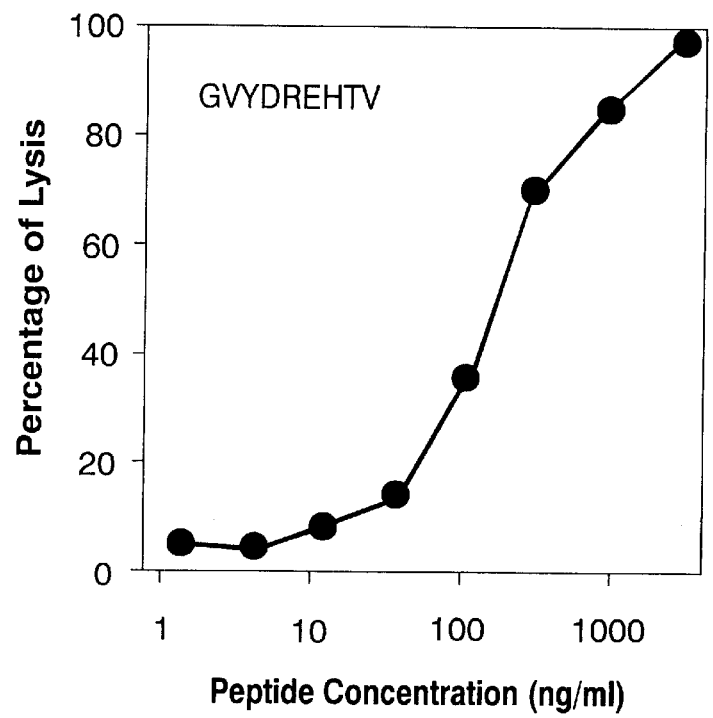

The sequence of the putative fragment of the MAGE-4 protein encoded by this region was screened for prediction of an HLA-A2 binding peptide with the software available at http://bimas.dcrt.nih.gov/molbio/hla_bind/index.html". Peptide GVYDGREHTV (MAGE-4 $_{230-239}$) (SEQ ID NO:44) had the highest score. It was synthesized and tested in a cytotoxicity assay at an effector to target ratio of 10:1. Peptide GVYDGREHTV (MAGE-4 $_{230-239}$) (SEQ ID NO:44) was found to sensitize autologous target cells to lysis by clone H4/13 (FIG. 5c).

Recognition by CTL Clone H4/13 of HLA-A2 Cells Expressing MAGE-4

Figure 5D:
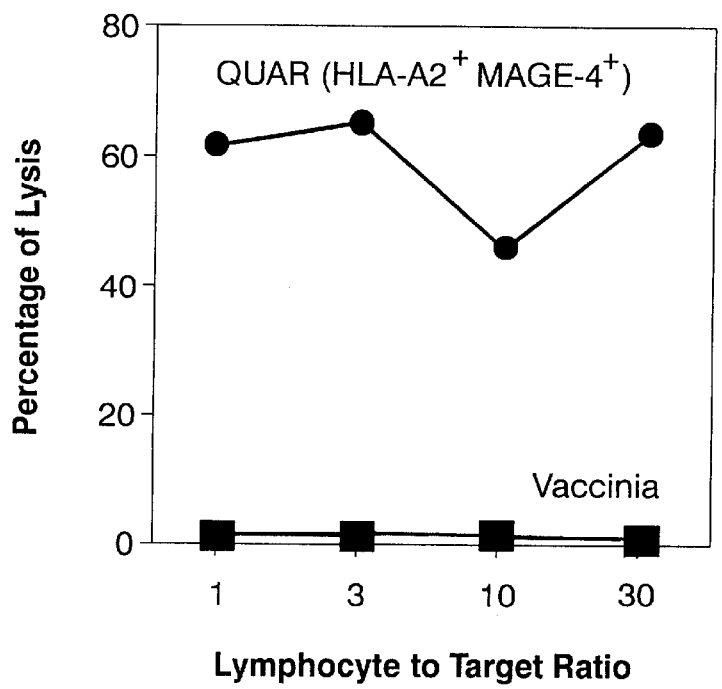

As indicated in FIG. 5d, CTL clone H4/13 was able to lyse HLA-A2 melanoma cell line QUAR (LB1751-MEL) t expressed MAGE-4.

We claim:

1. An isolated antigenic peptide consisting of DPARYEFLW (SEQ ID NO:42).

2. An isolated antigenic peptide consisting of GVYDGREHTV (SEQ ID NO:44).

3. A pharmaceutical composition comprising a peptide and a pharmaceutical carrier, wherein said peptide consists of DPARYEFLW (SEQ ID NO:42).

4. A pharmaceutical composition comprising a peptide and a pharmaceutical carrier, wherein said peptide consists of GVYDGREHTV (SEQ ID NO:44).

5. An isolated antigenic peptide consisting of SDPARYEFLWGPRALA (SEQ ID NO:39).

6. An isolated antigenic peptide consisting of SDPARYEFLW (SEQ ID NO:41).

7. A pharmaceutical composition comprising a peptide and a pharmaceutical carrier, wherein said peptide consists of SDPARYEFLWGPRALA (SEQ ID NO:39).

8. A pharmaceutical composition comprising a peptide and a pharmaceutical carrier, wherein said peptide consists of SDPARYEFLW (SEQ ID NO:41).

* * * * *

UNITED STATES PATENT AND TRADEMARK OFFICE
Certificate

Patent No. 6,407,063 B1                                                                                                Patented: June 18, 2002

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Rosalie Luiten, Brussels, Belgium; Marie-Therese Duffour, Brussels, Belgium; Nathalie Demotte, Brussels, Belgium; Pierre van der Bruggen, Brussels, Belgium; Guy R. Cornelis, Brussels, Belgium; Vincent Stroobant, Brussels, Belgium; Christophe Lurquin, Brussels, Belgium; Thierry Boon-Falleur, Brussels, Belgium; and Pascal Chaux, Brussels, Belgium.

Signed and Sealed this Eighteenth Day of September 2007.

WILLIAM R. DIXON, JR.
*Special Program Examiner*
Technology Center 1600

SEQUENCE LISTING

<160> NUMBER OF SEQ ID NOS: 45

<210> SEQ ID NO 1
<211> LENGTH: 9
<212> TYPE: PRT
<213> ORGANISM: Human MAGE-A1 peptide

<400> SEQUENCE: 1

Glu Ala Asp Pro Thr Gly His Ser Tyr
                  5

<210> SEQ ID NO 2
<211> LENGTH: 9
<212> TYPE: PRT
<213> ORGANISM: Human MAGE-A1 peptide

<400> SEQUENCE: 2

Ser Ala Tyr Gly Glu Pro Arg Lys Leu
                  5

<210> SEQ ID NO 3
<211> LENGTH: 9
<212> TYPE: PRT
<213> ORGANISM: Human MAGE-A3 peptide

<400> SEQUENCE: 3

Glu Val Asp Pro Ile Gly His Leu Tyr
                  5

<210> SEQ ID NO 4
<211> LENGTH: 9
<212> TYPE: PRT
<213> ORGANISM: Human MAGE-A3 peptide

<400> SEQUENCE: 4

Phe Leu Trp Gly Pro Arg Ala Leu Val
                  5

<210> SEQ ID NO 5
<211> LENGTH: 10
<212> TYPE: PRT
<213> ORGANISM: Human MAGE-A3 peptide

```
<400> SEQUENCE: 5

Met Glu Val Asp Pro Ile Gly His Leu Tyr
                5                   10

<210> SEQ ID NO 6
<211> LENGTH: 9
<212> TYPE: PRT
<213> ORGANISM: Human BAGE peptide

<400> SEQUENCE: 6

Ala Ala Arg Ala Val Phe Leu Ala Leu
                5

<210> SEQ ID NO 7
<211> LENGTH: 8
<212> TYPE: PRT
<213> ORGANISM: Human GAGE-1,2 peptide

<400> SEQUENCE: 7

Tyr Arg Pro Arg Pro Arg Arg Tyr
                5

<210> SEQ ID NO 8
<211> LENGTH: 10
<212> TYPE: PRT
<213> ORGANISM: Human RAGE peptide

<400> SEQUENCE: 8

Ser Pro Ser Ser Asn Arg Ile Arg Asn Thr
                5                   10

<210> SEQ ID NO 9
<211> LENGTH: 10
<212> TYPE: PRT
<213> ORGANISM: Human GnT-V peptide

<400> SEQUENCE: 9

Val Leu Pro Asp Val Phe Ile Arg Cys Val
                5                   10

<210> SEQ ID NO 10
<211> LENGTH: 9
<212> TYPE: PRT
<213> ORGANISM: Human MUM-1 peptide

<400> SEQUENCE: 10

Glu Glu Lys Leu Ile Val Val Leu Phe
                5

<210> SEQ ID NO 11
<211> LENGTH: 9
<212> TYPE: PRT
<213> ORGANISM: Human MUM-1 peptide

<400> SEQUENCE: 11

Glu Glu Lys Leu Ser Val Val Leu Phe
                5

<210> SEQ ID NO 12
<211> LENGTH: 10
<212> TYPE: PRT
<213> ORGANISM: Human CDK4 peptide

<400> SEQUENCE: 12
```

Ala Cys Asp Pro His Ser Gly His Phe Val
                5                  10

<210> SEQ ID NO 13
<211> LENGTH: 10
<212> TYPE: PRT
<213> ORGANISM: Human CDK4 peptide

<400> SEQUENCE: 13

Ala Arg Asp Pro His Ser Gly His Phe Val
                5                  10

<210> SEQ ID NO 14
<211> LENGTH: 9
<212> TYPE: PRT
<213> ORGANISM: Human -catenin peptide

<400> SEQUENCE: 14

Ser Tyr Leu Asp Ser Gly Ile His Phe
                5

<210> SEQ ID NO 15
<211> LENGTH: 9
<212> TYPE: PRT
<213> ORGANISM: Human -catenin peptide

<400> SEQUENCE: 15

Ser Tyr Leu Asp Ser Gly Ile His Ser
                5

<210> SEQ ID NO 16
<211> LENGTH: 9
<212> TYPE: PRT
<213> ORGANISM: Human Tyrosinase peptide

<400> SEQUENCE: 16

Met Leu Leu Ala Val Leu Tyr Cys Leu
                5

<210> SEQ ID NO 17
<211> LENGTH: 9
<212> TYPE: PRT
<213> ORGANISM: Human Tyrosinase peptide

<400> SEQUENCE: 17

Tyr Met Asn Gly Thr Met Ser Gln Val
                5

<210> SEQ ID NO 18
<211> LENGTH: 9
<212> TYPE: PRT
<213> ORGANISM: Human Tyrosinase peptide

<400> SEQUENCE: 18

Tyr Met Asp Gly Thr Met Ser Gln Val
                5

<210> SEQ ID NO 19
<211> LENGTH: 9
<212> TYPE: PRT
<213> ORGANISM: Human Tyrosinase peptide

<400> SEQUENCE: 19

Ala Phe Leu Pro Trp His Arg Leu Phe

<210> SEQ ID NO 20
<211> LENGTH: 9
<212> TYPE: PRT
<213> ORGANISM: Human Tyrosinase peptide

<400> SEQUENCE: 20

Ser Glu Ile Trp Arg Asp Ile Asp Phe
                 5

<210> SEQ ID NO 21
<211> LENGTH: 9
<212> TYPE: PRT
<213> ORGANISM: Human Tyrosinase peptide

<400> SEQUENCE: 21

Tyr Glu Ile Trp Arg Asp Ile Asp Phe
                 5

<210> SEQ ID NO 22
<211> LENGTH: 15
<212> TYPE: PRT
<213> ORGANISM: Human Tyrosinase peptide

<400> SEQUENCE: 22

Gln Asn Ile Leu Leu Ser Asn Ala Pro Leu Gly Pro Gln Phe Pro
                 5                  10                  15

<210> SEQ ID NO 23
<211> LENGTH: 15
<212> TYPE: PRT
<213> ORGANISM: Human Tyrosinase peptide

<400> SEQUENCE: 23

Asp Tyr Ser Tyr Leu Gln Asp Ser Asp Pro Asp Ser Phe Gln Asp
                 5                  10                  15

<210> SEQ ID NO 24
<211> LENGTH: 10
<212> TYPE: PRT
<213> ORGANISM: Human Melan-AMART-1 peptide

<400> SEQUENCE: 24

Glu Ala Ala Gly Ile Gly Ile Leu Thr Val
                 5                  10

<210> SEQ ID NO 25
<211> LENGTH: 9
<212> TYPE: PRT
<213> ORGANISM: Human Melan-AMART-1 peptide

<400> SEQUENCE: 25

Ile Leu Thr Val Ile Leu Gly Val Leu
                 5

<210> SEQ ID NO 26
<211> LENGTH: 9
<212> TYPE: PRT
<213> ORGANISM: Human gp100Pmel117 peptide

<400> SEQUENCE: 26

Lys Thr Trp Gly Gln Tyr Trp Gln Val
                 5

```
<210> SEQ ID NO 27
<211> LENGTH: 9
<212> TYPE: PRT
<213> ORGANISM: Human gp100Pmel117 peptide

<400> SEQUENCE: 27

Ile Thr Asp Gln Val Pro Phe Ser Val
                5

<210> SEQ ID NO 28
<211> LENGTH: 9
<212> TYPE: PRT
<213> ORGANISM: Human gp100Pmel117 peptide

<400> SEQUENCE: 28

Tyr Leu Glu Pro Gly Pro Val Thr Ala
                5

<210> SEQ ID NO 29
<211> LENGTH: 10
<212> TYPE: PRT
<213> ORGANISM: Human gp100Pmel117 peptide

<400> SEQUENCE: 29

Leu Leu Asp Gly Thr Ala Thr Leu Arg Leu
                5                   10

<210> SEQ ID NO 30
<211> LENGTH: 10
<212> TYPE: PRT
<213> ORGANISM: Human gp100Pmel117 peptide

<400> SEQUENCE: 30

Val Leu Tyr Arg Tyr Gly Ser Phe Ser Val
                5                   10

<210> SEQ ID NO 31
<211> LENGTH: 9
<212> TYPE: PRT
<213> ORGANISM: Human DAGE peptide

<400> SEQUENCE: 31

Leu Tyr Val Asp Ser Leu Phe Phe Leu
                5

<210> SEQ ID NO 32
<211> LENGTH: 12
<212> TYPE: PRT
<213> ORGANISM: Human MAGE-A6 peptide

<400> SEQUENCE: 32

Lys Ile Ser Gly Gly Pro Arg Ile Ser Tyr Pro Leu
                5                   10

<210> SEQ ID NO 33
<211> LENGTH: 31
<212> TYPE: DNA
<213> ORGANISM: Human MAGE-A1 primer

<400> SEQUENCE: 33
aaactgcaga tgtctcttga gcagaggagt c                              31

<210> SEQ ID NO 34
<211> LENGTH: 30
```

```
<210> SEQ ID NO 34
<211> LENGTH: 30
<212> TYPE: DNA
<213> ORGANISM: Human MAGE-A1 primer

<400> SEQUENCE: 34
aaactgcagt cagactccct cttcctcctc                                    30

<210> SEQ ID NO 35
<211> LENGTH: 32
<212> TYPE: DNA
<213> ORGANISM: Human MAGE-A4 primer

<400> SEQUENCE: 35
aaaaactgca gatgtcttct gagcagaaga gt                                 32

<210> SEQ ID NO 36
<211> LENGTH: 29
<212> TYPE: DNA
<213> ORGANISM: Human MAGE-A4 primer

<400> SEQUENCE: 36
aaaaaatcga ttcagactcc ctcttcctc                                     29

<210> SEQ ID NO 37
<211> LENGTH: 16
<212> TYPE: PRT
<213> ORGANISM: Human MAGE-A1 peptide

<400> SEQUENCE: 37

Asp Gly Arg Glu His Ser Ala Tyr Gly Glu Pro Arg Lys Leu Leu Thr
 1               5                  10                  15

<210> SEQ ID NO 38
<211> LENGTH: 16
<212> TYPE: PRT
<213> ORGANISM: Human MAGE-A1 peptide

<400> SEQUENCE: 38

Gln Val Pro Asp Ser Asp Pro Ala Arg Tyr Glu Phe Leu Trp Gly Pro
 1               5                  10                  15

<210> SEQ ID NO 39
<211> LENGTH: 16
<212> TYPE: PRT
<213> ORGANISM: Human MAGE-A1 peptide

<400> SEQUENCE: 39

Ser Asp Pro Ala Arg Tyr Glu Phe Leu Trp Gly Pro Arg Ala Leu Ala
 1               5                  10                  15

<210> SEQ ID NO 40
<211> LENGTH: 16
<212> TYPE: PRT
<213> ORGANISM: Human MAGE-A4 peptide

<400> SEQUENCE: 40

Gly Ser Asn Pro Ala Arg Tyr Glu Phe Leu Trp Gly Pro Arg Ala Leu
 1               5                  10                  15

<210> SEQ ID NO 41
<211> LENGTH: 10
<212> TYPE: PRT
<213> ORGANISM: Human MAGE-A1 peptide

<400> SEQUENCE: 41
```

Ser Asp Pro Ala Arg Tyr Glu Phe Leu Trp
 1               5                   10

<210> SEQ ID NO 42
<211> LENGTH: 9
<212> TYPE: PRT
<213> ORGANISM: Human MAGE-A1 peptide

<400> SEQUENCE: 42

Asp Pro Ala Arg Tyr Glu Phe Leu Trp
 1               5

<210> SEQ ID NO 43
<211> LENGTH: 130
<212> TYPE: DNA
<213> ORGANISM: Human MAGE-A4 primer

<400> SEQUENCE: 43
tgatgggagg gagcacactg tctatgggga gcccaggaaa ctgctcaccc aagattgggt      60
gcaggaaaac tacctggagt accggcaggt acccggcagt aatcctgcgc gctatgagtt     120
cctgtggggt                                                            130

<210> SEQ ID NO 44
<211> LENGTH: 10
<212> TYPE: PRT
<213> ORGANISM: Human MAGE-A4 peptide

<400> SEQUENCE: 44

Gly Val Tyr Asp Gly Arg Glu His Thr Val
 1               5                   10

<210> SEQ ID NO 45
<211> LENGTH: 961
<212> TYPE: DNA
<213> ORGANISM: Human MAGE-A4 partial

<400> SEQUENCE: 45
agtcatcatg tcttctgagc agaagagtca gcactgcaag cctgaggaag gcgttgaggc      60
ccaagaagag gccctgggcc tggtgggtgc acaggctcct actactgagg agcaggaggc     120
tgctgtctcc tcctcctctc tctggtccc tggcaccctg gaggaagtgc ctgctgctga     180
gtcagcaggt cctcccccaga gtcctcaggg agcctctgcc ttaccaacta ccatcagctt     240
cacttgctgg aggcaaccca atgagggttc cagcagccaa gaagaggagg ggccaagcac     300
ctcgcctgac gcagagtcct tgttccgaga agcactcagt aacaaggtgg atgagttggc     360
tcattttctg ctccgcaagt atcgagccaa ggagctggtc acaaaggcag aaatgctgga     420
gagagtcatc aaaaattaca agcgctgctt cctgtgatc ttcggcaaag cctccgagtc      480
cctgaagatg atctttggca ttgacgtgaa ggaagtggac cccgccagca cacctacac      540 ccttgtcacc tgcctgggcc tttcctatga tggcctgctg ggtaataatc agatcttcc      600 caagacaggc cttctgataa tcgtcctggg cacaattgca atggagggcg acagcgcctc     660
tgaggaggaa atctgggagg agctgggtgt gatgggggtg tatgatggga gggagcacac     720
tgtctatggg gagcccagga aactgctcac ccaagattgg gtgcaggaaa actacctgga     780

```
-continued gtaccggcag gtacccggca gtaatcctgc gcgctatgag ttcctgtggg gtccaagggc    840
tctggctgaa accagctatg tgaaagtcct ggagcatgtg gtcagggtca atgcaagagt    900
tcgcattgcc tacccatccc tgcgtgaagc agctttgtta gaggaggaag agggagtctg    960
a                                                                    961
```